US008017835B2

(12) United States Patent
Chappell et al.

(10) Patent No.: US 8,017,835 B2
(45) Date of Patent: Sep. 13, 2011

(54) TRANSFORMED PLANTS ACCUMULATING TERPENES

(75) Inventors: Joe Chappell, Lexington, KY (US); Shuiqin Wu, Lexington, KY (US); Michel Schalk, Collonges-Sous-Saleve (FR); Athony Clark, West Windsor, NJ (US)

(73) Assignee: University of Kentucky Research Foundation, Lexington, KY (US)

( * ) Notice: Subject to any disclaimer, the term of this patent is extended or adjusted under 35 U.S.C. 154(b) by 681 days.

(21) Appl. No.: 11/911,660

(22) PCT Filed: Apr. 18, 2006

(86) PCT No.: PCT/IB2006/051198
§ 371 (c)(1),
(2), (4) Date: Apr. 25, 2008

(87) PCT Pub. No.: WO2006/111924
PCT Pub. Date: Oct. 26, 2006

(65) Prior Publication Data
US 2009/0123984 A1 May 14, 2009

(30) Foreign Application Priority Data
Jun. 16, 2005 (EP) ..................................... 05105281

(51) Int. Cl.
C12N 15/29 (2006.01)
C12N 15/31 (2006.01)
C12N 15/52 (2006.01)
C12N 15/82 (2006.01)

(52) U.S. Cl. ...... 800/288; 800/298; 435/193; 435/320.1

(58) Field of Classification Search .................... None
See application file for complete search history.

(56) References Cited

U.S. PATENT DOCUMENTS

| 7,091,027 B1 | 8/2006 | Wallaart et al. ............... 435/232 |
| 7,622,288 B2 * | 11/2009 | Schalk .......................... 435/193 |
| 2004/0161819 A1 | 8/2004 | Aharoni et al. ............... 435/69.1 |

FOREIGN PATENT DOCUMENTS

| EP | 1 063 297 A1 | 12/2000 |
| WO | WO 91/13078 | 9/1991 |
| WO | WO 00/12725 | 3/2000 |
| WO | WO 00/22150 | 4/2000 |
| WO | WO 02/33060 A2 | 4/2002 |
| WO | WO 02/064764 A2 | 8/2002 |
| WO | WO 2004/031376 A2 | 4/2004 |
| WO | WO 2005/052163 A2 | 6/2005 |

OTHER PUBLICATIONS

Chen D. et al. Plant Science (2000) vol. 155; pp. 179-185.*
Brodelius, M. et al. Eur. J. Biochem. (2000) vol. 269; pp. 3570-3577.*
Aharoni, A. et al. Plant Cell (Dec. 2003); vol. 15; pp. 2866-2884.*
Asaph Aharoni et al., XP002355234, "Terpenoid Metabolism in Wild-Type and Transgenic *Arabidopsis* Plants", Plant Cell, vol. 15, No. 12, pp. 2866-2884 (2003).
Andrea Hemmerlin et al., XP002407595 "Enzymes Encoded by the Farnesyl Diphosphate Synthase Gene Family in the Big Sagebrush *Artemisia Tridentata* Ssp.Spiciformis." Journal of Biological Chemistry, vol. 278, No. 34, pp. 32132-32140 (2003).
H. Nakashita et al., XP009056668, "Introduction of Bacterial Metabolism Into Higher Plants by Polycistronic Transgene Expression", Bioscience Biotechnology Biochemistry, vol. 65, No. 7, pp. 1688-1691 (2003).
Maria Brodelius et al., XP002407596, "Fusion of Farnesyldiphosphate Synthase and Epi-Aristolochene Synthase, A Sesquiterpene Cyclase Involved in Capsidiol Biosynthesis in *Nicotiana Tabacum*" European Journal of Biochemistry, vol. 269, No. 14, pp. 3570-3577 (2002).
Da-Hua Chen et al., XP002305638, "Expression of a Chimeric Farnesyl Diphosphate Synthase Gene in *Artemisia Annua* L. Transgenic Plants Via *Agrobacterium Tumefaciens*-Mediated Transformation", Plant Science, vol. 155, No. 2, pp. 179-185 (2000).
Asaph Aharoni et al., XP002355235, "Gain and Loss of Fruit Flavor Compounds Produced by Wild and Cultivated Strawberry Species" Plant Cell, vol. 16, No. 11, pp. 3110-3131 (2004).
R. Bock, XP001084937, "Transgenic Plastids in Basic Research and Plant Biotechnology" Journal of Molecular Biology, vol. 3, No. 312, pp. 425-438 (2001).

* cited by examiner

*Primary Examiner* — Russell Kallis
(74) *Attorney, Agent, or Firm* — Winston & Strawn LLP

(57) ABSTRACT

The present invention relates to transformed plants with an altered terpene content, preferably over-accumulating a mono- or sesqui-terpene. By transformation of plants with genes encoding terpene synthases (TS), and prenyl transferases (PRT), plants accumulating at least 1000 ng/per g of fresh leaf of a specific terpene were obtained. The present invention provides an advantageous system for production of terpenes in that any desired mono- or sesqui-terpene at the choice of the skilled person can be produced in plants. Preferably, the transformed plants contain at least one recombinant plastid targeted TS and PRT.

10 Claims, 20 Drawing Sheets

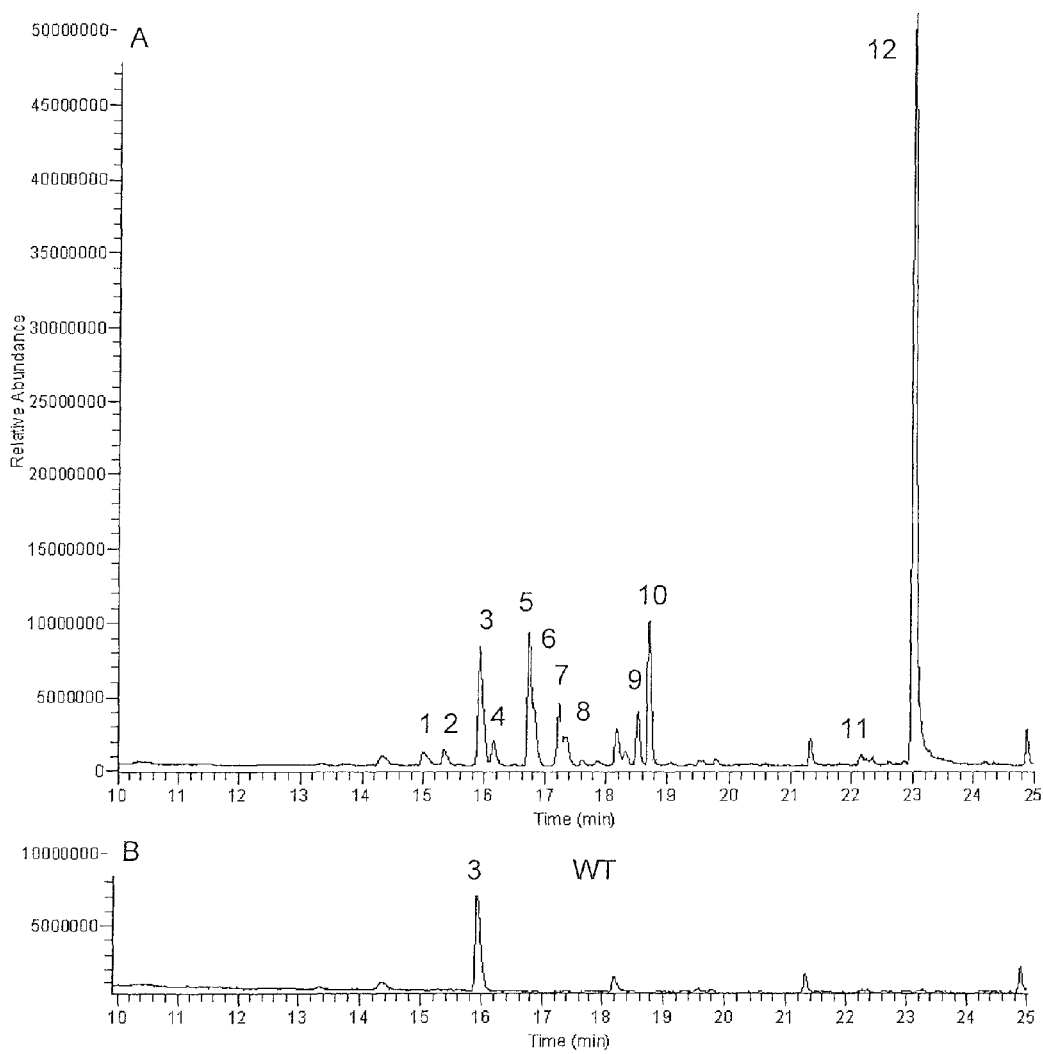
Figure 1 (A and B)

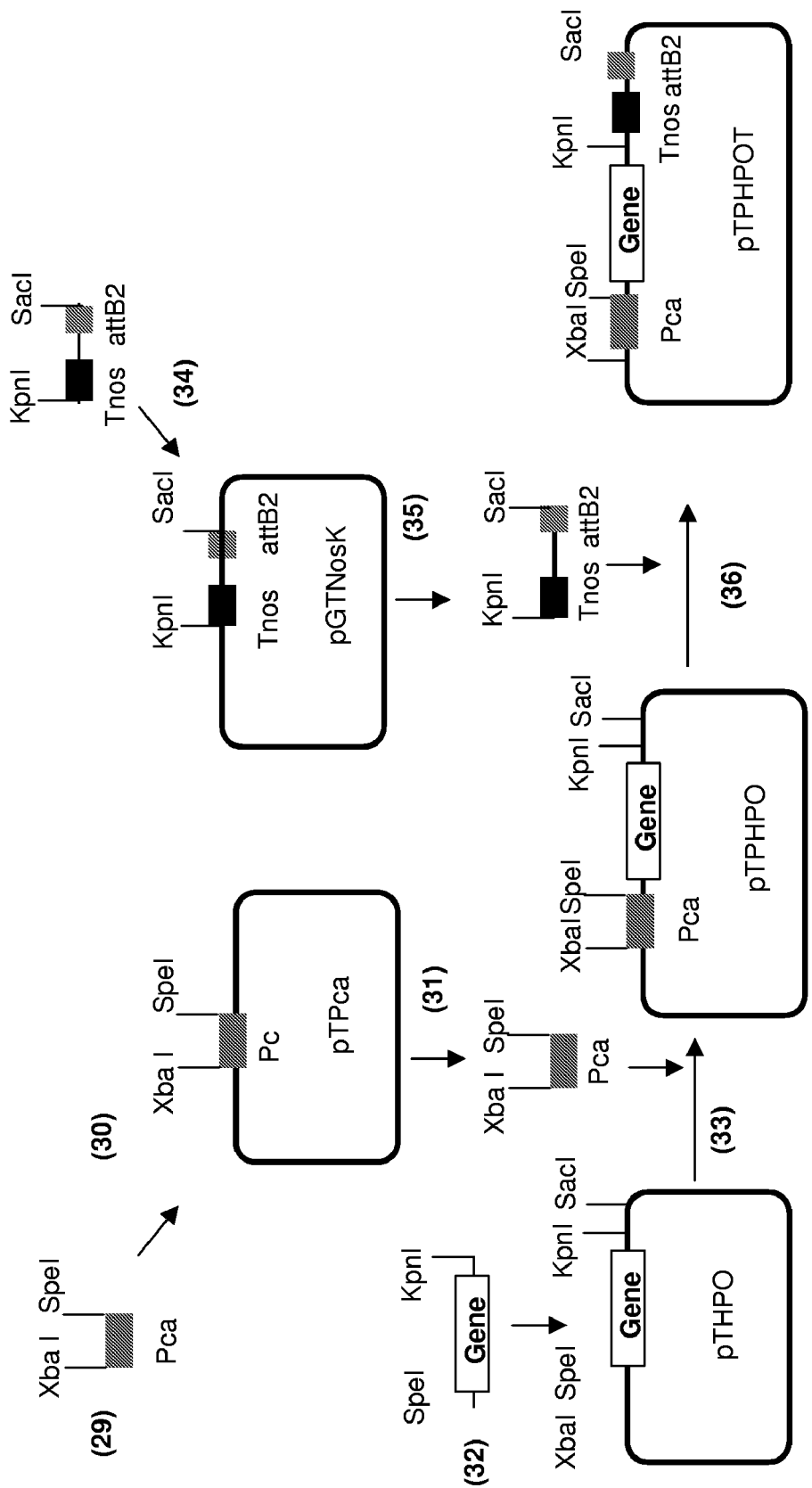
Figure 13 part I

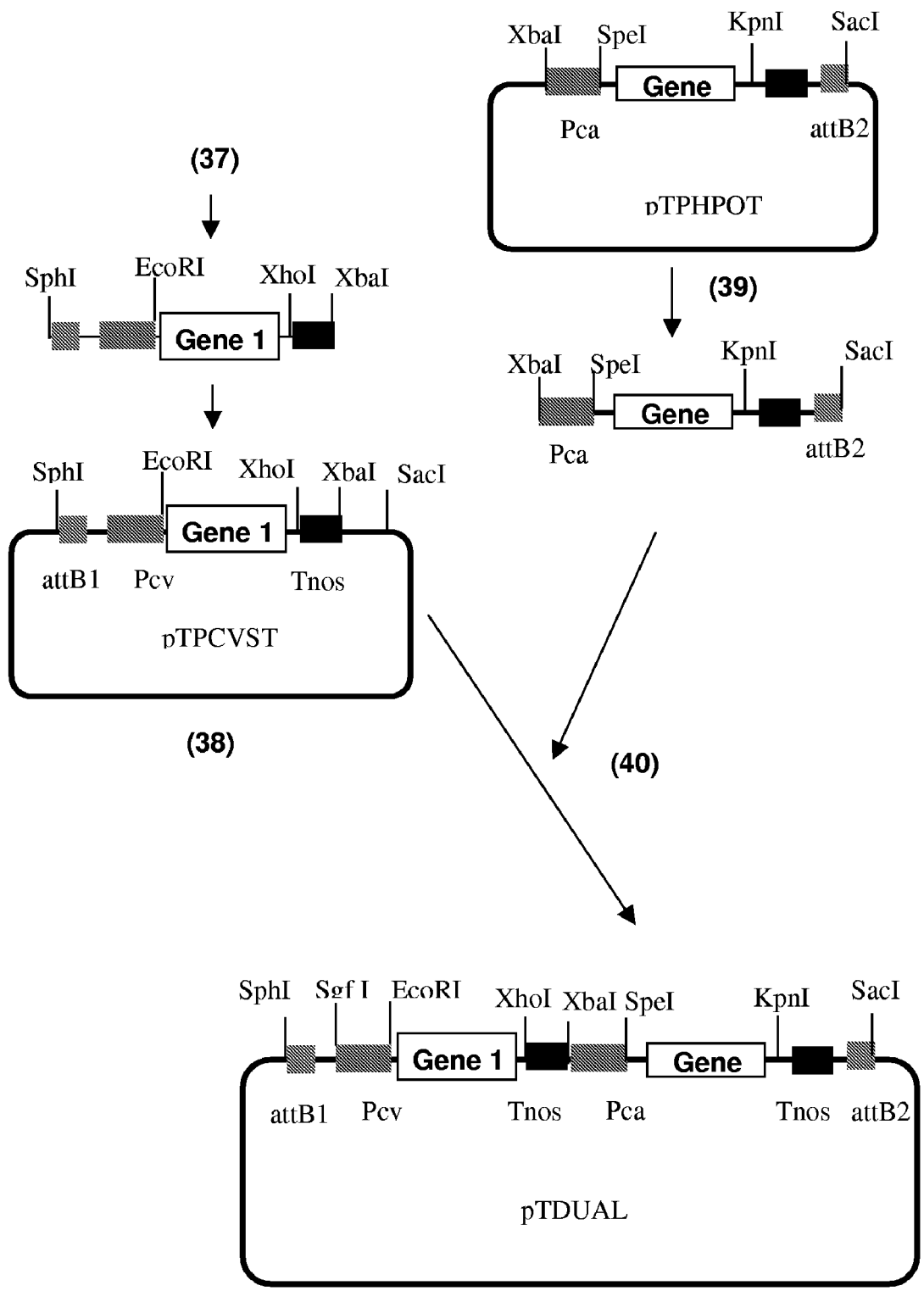
Figure 13 part II

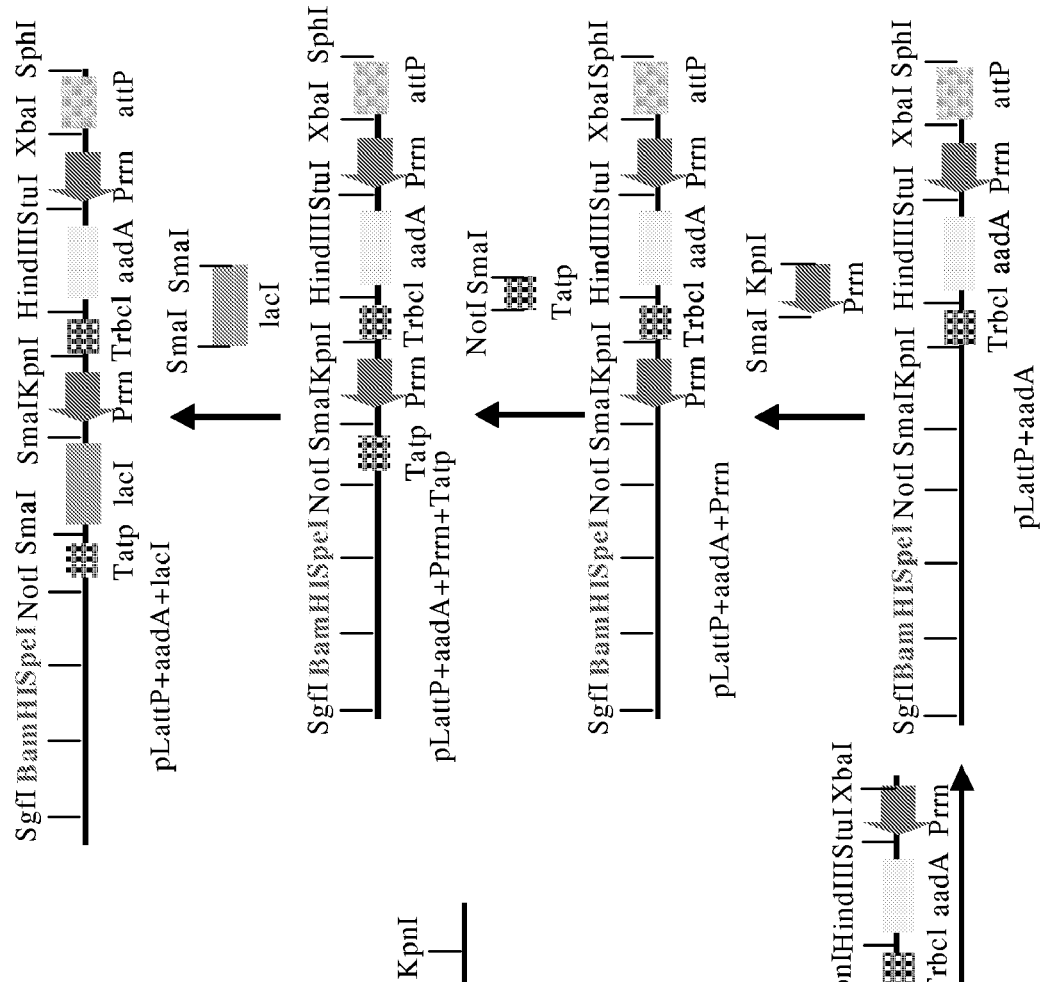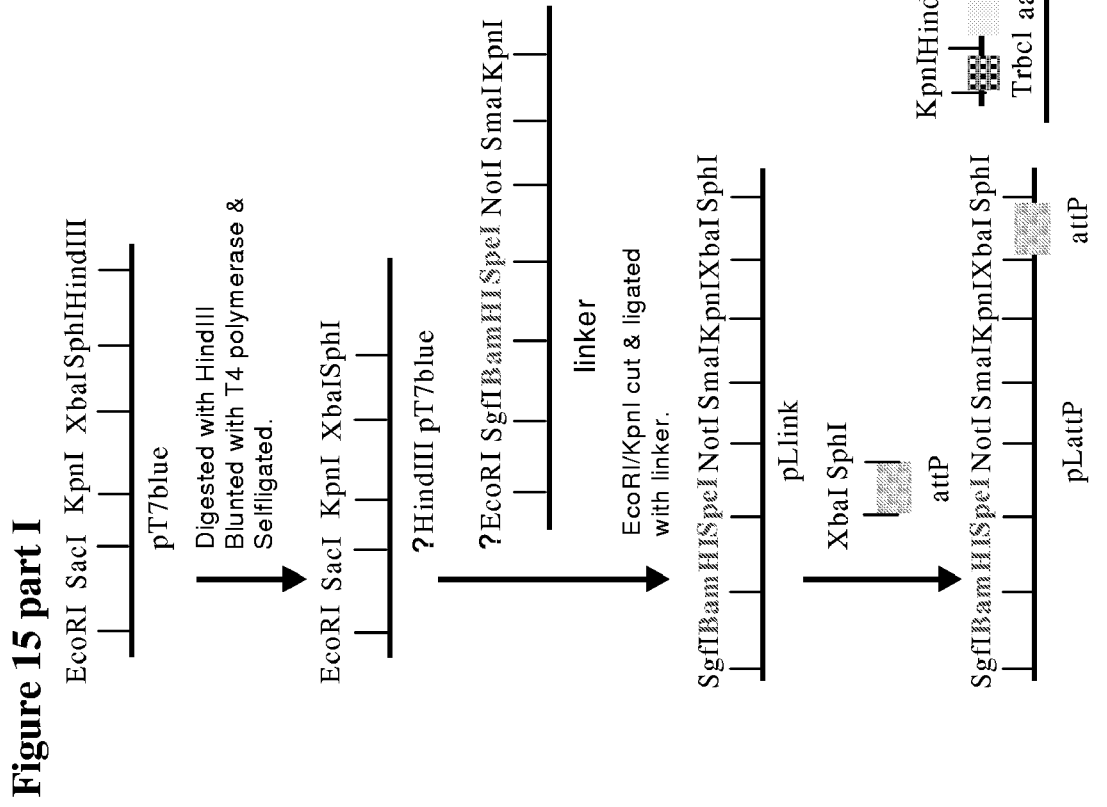
Figure 15 part I

Figure 15 part II
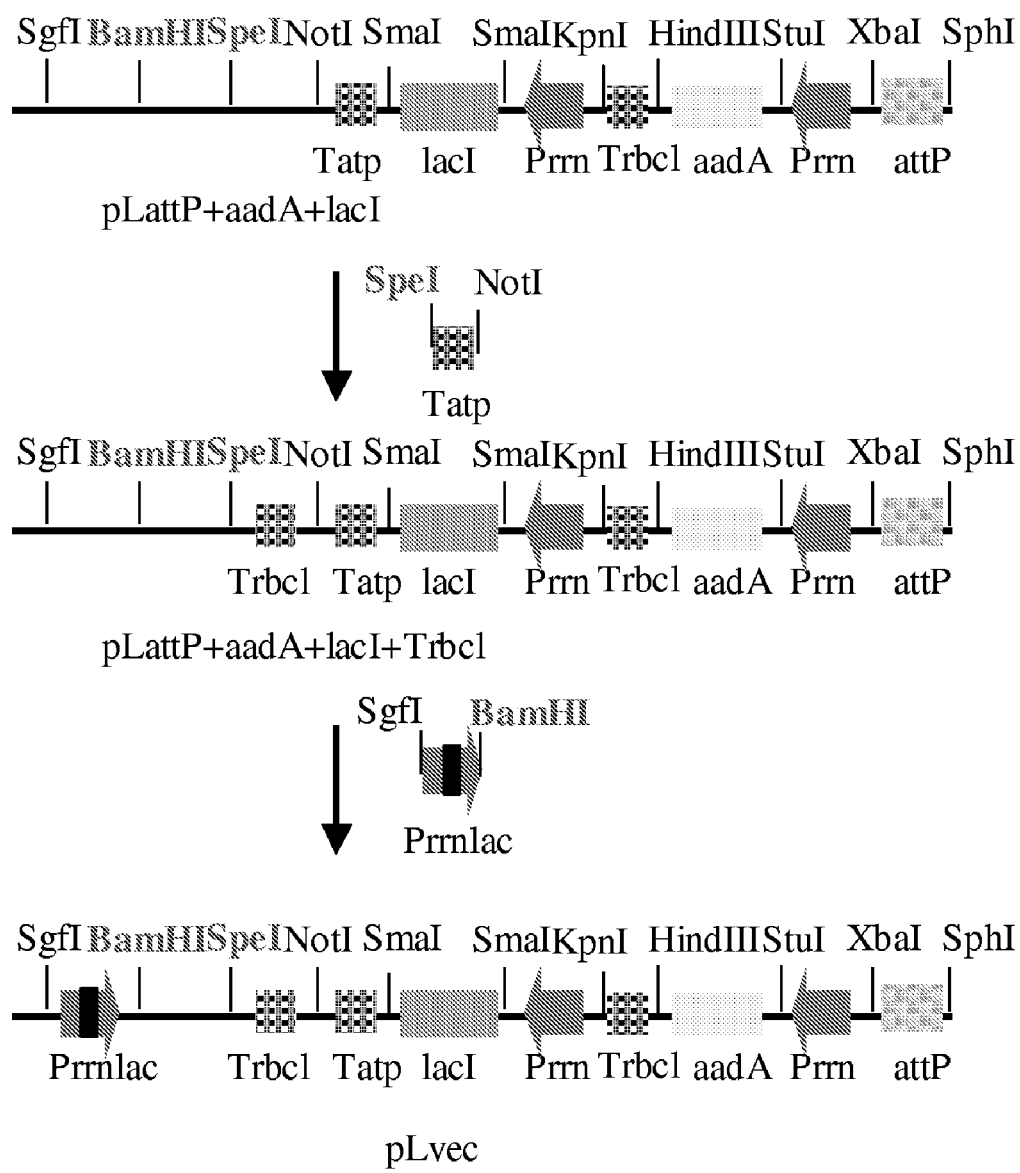

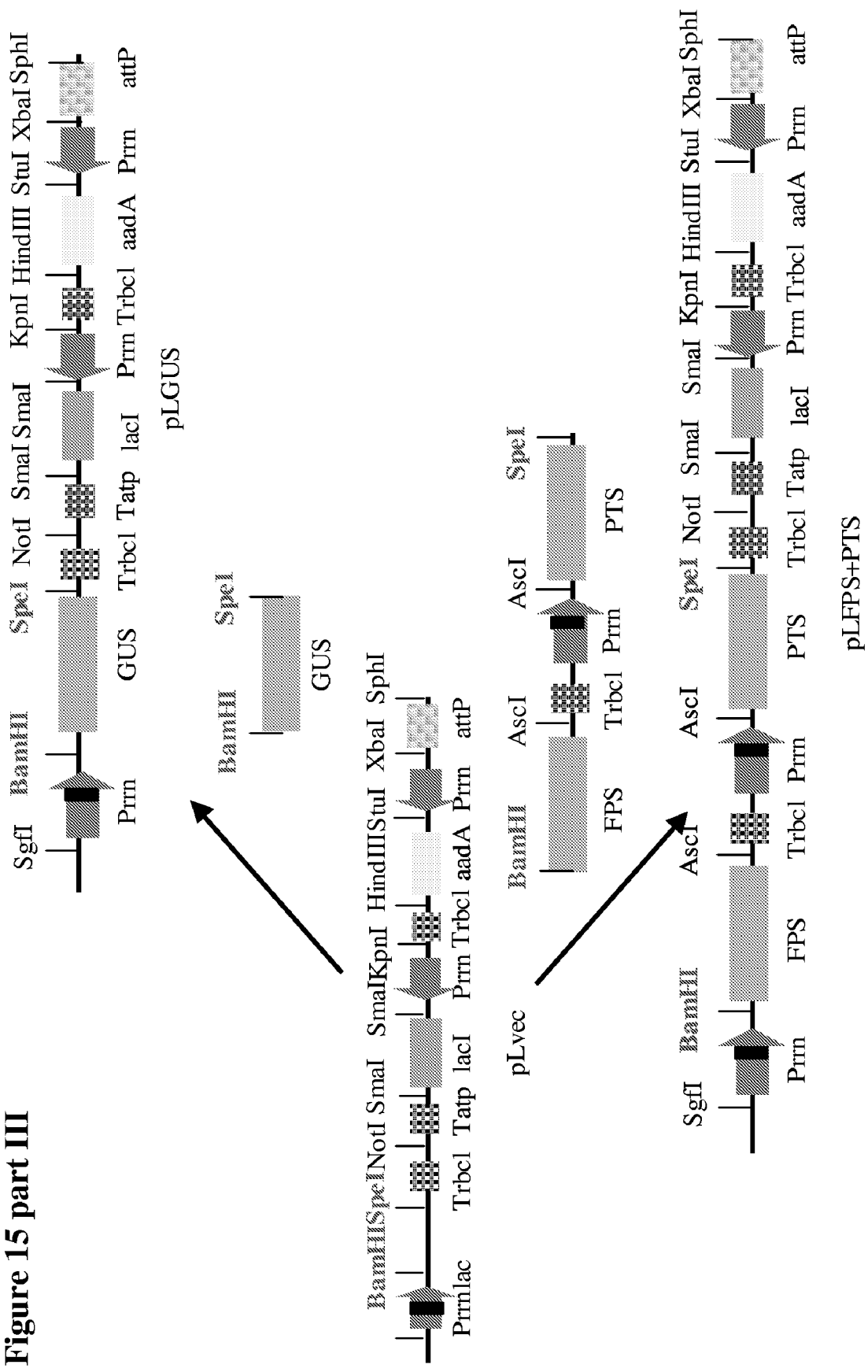
Figure 15 part III

TRANSFORMED PLANTS ACCUMULATING TERPENES

TECHNICAL FIELD

The present invention relates to transformed plants over-accumulating a specific mono- or sesquiterpene. The present invention further relates to a transformed plant with an altered content of a specific terpene, a vector comprising at least one nucleotide sequence encoding a prenyl transferase (PRT) and/or a mono- or sesquiterpene synthase (TS), methods for altering the content of specific terpenes in a plant, a method for increasing the content of specific terpenes in a plant, a method of producing a specific terpene and the use of at least one nucleotide sequence for producing plants having an altered terpene content.

BACKGROUND OF THE INVENTION AND PROBLEM TO BE SOLVED

Terpenes and terpenoids are found in most organisms. Their important commercial value, which is constantly increasing, is linked to the diverse range of bioactivities and functionalities encompassed by different terpenes. Accordingly, many vitamins, hormones, insect repellents, drugs, flavors and fragrances are found amongst this very large class of compounds, which all are made starting from units of 5 carbons called isoprene units.

Terpenes can be classified by the number of isoprene units present in their structure: monoterpenes ($C_{10}$), sesquiterpenes ($C_{15}$), diterpenes ($C_{20}$), triterpenes ($C_{30}$), tetraterpenes ($C_{40}$) and polyterpenes ($C_n$, n equal to or greater than 45 carbons). The plant kingdom contains a high diversity of mono- and sesquiterpenes representing thousands of different structures.

The chemical synthesis of higher terpenes such as sesqui- and diterpenes is very complex and environmentally acceptable processes for their preparation have not yet been realized. Therefore, it is a first objective of the present invention to provide methods for efficiently producing or accumulating specific terpenes while avoiding multiple-step chemical synthesis.

Studies on the biosynthetic pathway of terpenes revealed that the common $C_5$-precursor to all terpenes is isopentenyl diphosphate (IPP). Two distinct pathways for IPP biosynthesis coexist in the plants. The mevalonate pathway (MVA) is found in the cytosol in association with the endoplasmic reticulum and the non-mevalonate pathway, also called deoxyxylulose or methyl-D-erythritol phosphate pathway (DOXP/MEP) is found in the plastids of higher plants. The starting products, the enzymes involved and the catalysed reactions are different in both pathways, and, in the cells of higher plants they operate in parallel and complement each other. Accordingly, the MVA pathway in the cytoplasm is responsible for the biosynthesis of sterols, sesquiterpenes, and polyterpenes, whereas the plastid (MEP pathway) provides $C_5$-units for the synthesis of monoterpenes, diterpenes, for example kaurene ($C_{20}$), and polyterpenes, for example carotenoids ($C_{40}$) and plastoquinone-9 ($C_{45}$).

Following the synthesis of IPP, it is repetitively condensed by prenyl transferases (PRT) to form the acyclic prenyl diphosphate terpene precursors for each class of terpenes, that is, geranyl-diphosphate (GPP) for the monoterpenes, farnesyl-diphosphate (FPP) for the sesquiterpenes, geranylgeranyl-diphosphate (GGPP) for the diterpenes. These precursors in turn serve as substrate for the terpene synthases or cyclases, which are specific for each class of terpene, e.g. monoterpene, sesquiterpene or diterpene synthases. Terpene synthases can catalyze complex multiple step cyclizations to form the large diversity of carbon skeleton of the terpene compounds.

Attempts have been made to isolate specific terpene synthases and WO 2004/031376 reports the isolation of the genes encoding cubebol, valencene and germacrene synthases. When E. coli cells were transformed with plasmids containing these genes, the corresponding fragrance compounds could be found in the cultivating medium. Generally, in view prior art concerned with heterologous expression of terpene synthases, it is an objective to provide means and methods for accumulating specific terpenes in still higher amounts.

In U.S. Pat. No. 5,589,619, U.S. Pat. No. 5,365,017, U.S. Pat. No. 5,349,126 and U.S. Pat. No. 5,349,126 processes for increasing squalene and sterol accumulation in transgenic plants are disclosed. These references, however, are silent as to how the accumulation of other classes of terpenes, such as mono-sesqui- and diterpenes could be increased.

The preparation of transgenic plants is also the subject of U.S. Pat. No. 6,841,717, which relates to genes associated with the MEP-pathway. This reference teaches a DNA molecule encoding an HMBPP-Synthase (GCPE protein), which was linked to a chloroplast transit peptide and was thus used to produce a transgenic plant. While this reference deals with the accumulation of tocopherol substrates, it is silent how other terpene compounds can effectively be accumulated.

In U.S. Pat. No. 6,653,530 a method for increasing carotenoid production in seed is disclosed, in which a host plant is transformed with nucleic acid sequence of Erwinia uredora encoding a phytoene synthase.

WO 00/22150 discloses methods creating or enhancing resistance to insects in plants by expressing the monoterpenes synthases limonene-, carveol and S-linool synthases in plants transformed with nucleotide sequences encoding these enzymes.

WO 02/33060 A2 discloses nucleic acid sequences and methods for producing plants and seeds having altered tocopherol content and compositions.

In WO 91/13078 DNA sequences encoding various enzymes of Erwinia herbicola are disclosed. Transformed host organisms producing GGPP and various carotenoids are also mentioned.

EP 1 063 297 provides cDNA sequences coding for farnesyl diphosphate synthase and transgenic plants expressing heterologous farnesyl diphosphate synthase.

WO 02/064764 discloses isolated or recombinent nucleic acid sequences capable of synthesizing a monoterpene linalool and/or a sesquiterpene nerolidol when contacted with the respective precursor. In example 11, the difficulty of producing sesquiterpenes in transgenic plants is acknowledged, and no concrete results in this respect are presented.

Similarly, in a publication of Aharoni et al. "Terpenoid Metabolism in Wild-Type and Transgenic Arabidobsis Plants", the Plant cell, Vol. 15, 2866-2884, only very low levels of nerolidol were synthesized by linalool/nerolidol synthase targeted to the plastids.

The present inventors address the problem of producing or accumulating a specific, selected terpene. Preferably, a method is provided, which is suitable to produce not only a pre-determined, but any terpene of interest. The objective is thus to provide a system which allows, for example, the accumulation of any of the above-indicated sesquiterpenes, such as cubebol, valencene, germacrene, patchoulol, but which is also suitable to accumulate other terpenes. This problem has so far not been solved by the prior art, the latter basically suggesting recombinant organisms having modified properties in the MVA or MEP pathway, and observing that certain terpene end products get accumulated.

A further objective of the present invention is to provide means for generating any selected terpene, preferably a sesquiterpene, in a stereochemically pure form and with a reliable and cost effective production platform.

An important problem addressed by the present inventors is the increased accumulation of a selected terpene, preferably a sesquiterpene, in plants. In the prior art, yields of a maximum of about 10 µg terpene per g fresh weight plant material are reported. In particular with respect to sesquiterpenes, accumulation remains particularly low, in general in the order of micro-grams or below. It is thus an objective of the present invention to provide a possibility of accumulating more significant amounts of any terpene at the choice of the skilled person in a plant, and in particular of a sesquiterpene. Preferably, the plant can easily be cultivated. It is a further objective to accumulate the terpene in plant organs that provide a high biomass with respect to the total weight of the adult plant.

Another objective of the present invention is to provide plants accumulating sufficient amounts of terpenes for inhibiting growth of plant pathogens and attack by herbivores.

SUMMARY OF THE INVENTION

Remarkably, the present inventors were able to transform organisms with genes encoding a farnesyl diphosphate synthase (FPS) and a specific mono- or sesquiterpene synthase targeted to the plastids of the plant and obtained high yield of the terpene that is synthesized by the terpene synthase (TS). For the first time, enzymes of the isoprenoid biosynthetic pathway typically present in the cytosol could be directed to another cell compartment, the plastid, and, surprisingly, the amount of selected terpene compounds could be increased by exploiting precursors of a different pathway. An important advantage of the present invention is that any desired terpene can be accumulated in any plant, if the nucleotide sequence encoding the synthase of the selected terpene is known or susceptible to be isolated. This is possible by targeting to the plastids of a plant at least two gene products, that is a TS and the enzyme capable of synthesising the direct precursor for the TS, a prenyl transferase (PRT).

Accordingly, the present invention provides, in a first aspect, a transformed plant over-accumulating a specific terpene, preferably a mono- or sesquiterpene.

In a further aspect, the present invention provides a transformed plant with an altered content of a specific terpene, said transformed plant comprising structural genes comprising at least one nucleotide sequence encoding a prenyltransferase (PRT) and a terpene synthase (TS) targeted to the plastids of the plant.

In another aspect, the present invention provides a transformed plant accumulating a sesquiterpene, which is transformed to comprise at least one nucleotide sequence encoding a farnesyl diphosphate synthase (FPS) and a sesquiterpene synthase targeted to the plastid of the plant.

In a further aspect, the present invention provides a vector comprising at least one nucleotide sequence encoding a PRT and/or a TS, or a fusion protein of a PRT and a TS, said nucleotide sequence further comprising a plastid targeting sequence linked in frame to the nucleotide sequence encoding the PRT, the TS, and/or the fusion protein.

In still further aspects, the present invention provides methods for altering the content of specific terpenes in a plant and for increasing the content of specific terpenes in a plant, the methods comprising the steps of transforming plant material with at least one DNA construct comprising at least one nucleotide sequence encoding a farnesyl diphosphate synthase, FPS or, if the terpene is a monoterpene, a geranyl diphosphate synthase, and a sesquiterpene synthase, or, a monoterpene synthase, respectively, and, regenerating the transformed plant from the transformed plant material.

In still other aspects, the present invention provides a method of producing a specific terpene, the method comprising the step of isolating the terpene from the plant according to the invention, and, the use of at least one nucleotide sequence encoding a plastid targeted functional PRT and/or TS for producing plants having an altered terpene content.

The present invention also relates to a method of producing a sesquiterpene, the method comprising the step of cultivating the plant of the present invention.

BRIEF DESCRIPTION OF THE DRAWINGS

FIG. 13 part I and II schematically show the construction of pTDUAL helper vector (FIG. 9 B).

FIG. 15 parts I-III show the details of the preparation of a vector for transformation of plant plastidic DNA with genes encoding sesquiterpene and farnesyl diphosphate synthases.

DETAILED DESCRIPTION OF THE INVENTION

Figure 1:
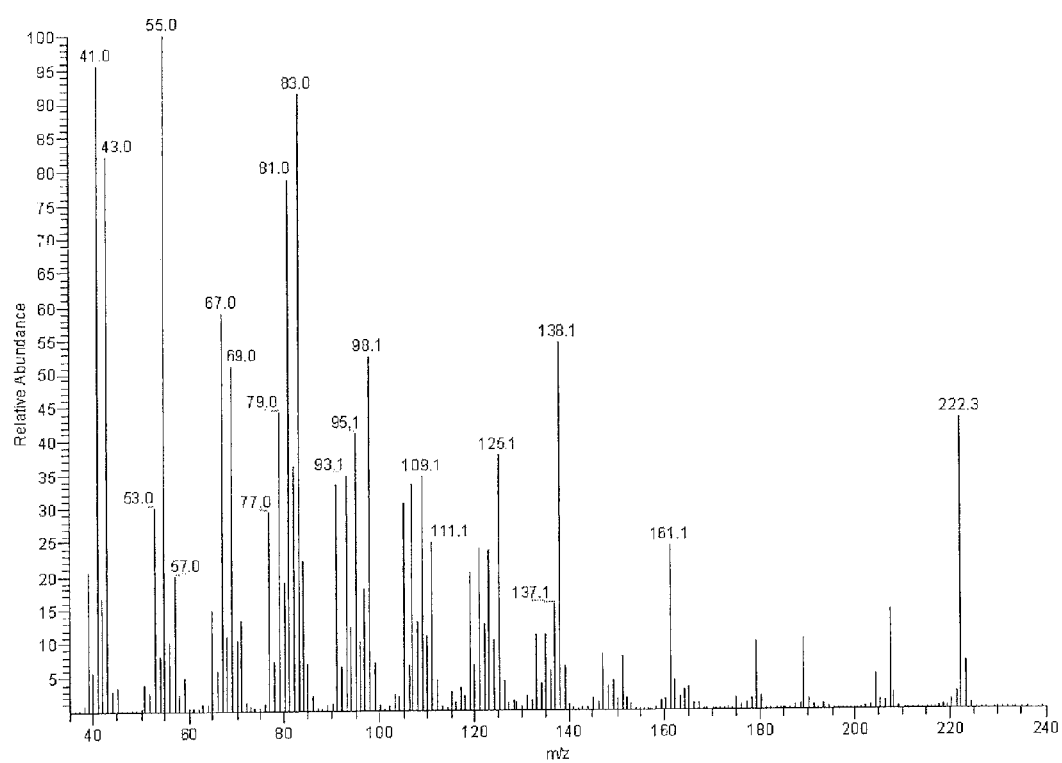
FIG. 1 shows GC-MS analysis of a control tobacco line (WT) and one transformed with a construct comprising plastid targeted genes encoding a sesquiterpene (patchoulol) synthase and a farnesyl diphosphate synthase (tpPTS+tpFPS). Peak 12 in chromatogram A is analysed by MS in part C and could be identified as patchoulol by comparison to authentic patchoulol (D). Peak 3 was used as an internal standard (3-α-cedrene).
Figure 1:
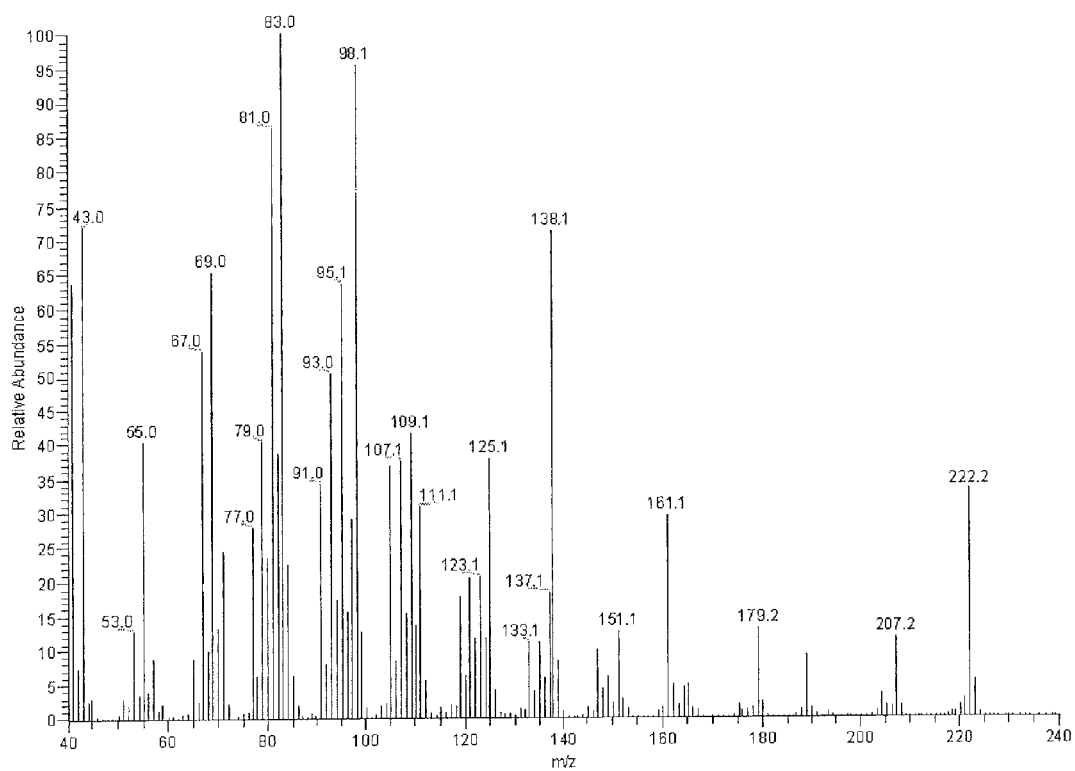

The present invention relates to a transformed plant accumulating a specific mono-, or sesquiterpene. The invention also relates to transformed plants with an altered content of a specific terpene, the plant comprising structural genes targeted to the plastids of the plant.

A "transformed plant", for the purpose of the present invention, is a plant, which was subjected to genetic engineering. A "transformed plant", includes asexually (vegetative) and sexually derived material from an individual plant that has been transformed. For example, plants obtained by crossing of a plant having individually been transformed with an untransformed plants is encompassed by the present invention, if the progeny contains at least a nucleotide sequence encoding a PRT and a terpene synthase targeted to the plastid of the plant, according to the invention. The plant may be any plant, preferably, it is a plant which is suitable to be transformed according to the present invention. Preferably, the plant is a plant, which naturally produces high amounts of terpenes. For example, the plant is selected from the family of Solanaceae, Poaceae or Lamiaceae. For example, the plant is selected from the genera *Nicotiana, Solanum, Sorghum, Arabidopsis, Medicago* (alfalfa), *Gossypium* (cotton), *Brassica* (rape). Preferably, the plant belongs to the species of *Nicotiana tabacum*.

While the present invention is preferably related to plants, its concepts can equally well be used with other organelle-containing organisms. For example, the present invention also applies to algae and fungi. Preferably, it applies to plastid-containing organisms such as algae and plants.

The terms "altered content of a specific terpene" or "accumulating a specific terpene" means the content of a specific terpene of a plant transformed according to the present invention is higher than the content of the same terpene in the same plant not so transformed. The invention thus covers two main situations: First, the invention relates to plants, the wild-type of which does not produce the terpene of specific interest. By transformation according to the invention, these plants will accumulate the terpene of interest and thus have an altered content of the specific terpene. According to another situation encompassed by the invention, a plant already produces the terpene of interest. By transformation, the plant will produce more of the specific terpene and thus have an altered terpene content.

Similarly, the term "accumulating" or "over-accumulating" refers to a higher content of a specific terpene in a transformed plant if compared to the same plant not so transformed.

Accordingly, the term "expression" "or over-expression" of a PRT and/or a TS gene refers to plants having a higher content of PRT and/or TS RNA in any plant organs, for example leaves, than compared to a control, non-transformed plant.

A "terpene", is a hydrocarbon based on or composed of isoprene units ($C_5H_8$), which may be acyclic or cyclic.

As used herein, a "monoterpene" is a terpene based on a $C_{10}$ structure and includes monoterpene derivatives. Examples are menthol, limonene, α-pinene, β-pinene, S-linalool, just to mention specific examples for illustration.

As used herein, a "sesquiterpene" is a terpene based on a $C_{15}$ structure. Examples are cyclosativene, cyclocopacamphene, cyclocopacamphenol epimers, cyclocopacamphenal epimers, cyclocopacamphenic acid epimers, cis-α-bergamotene, trans-α-bergamotene, (+)-epi-β-santalene, β-bisabolene, and trans-γ-bisabolene.

The terms "terpene", "mono"-, and "sesquiterpenes", for the purpose of the present invention, also includes terpene derivatives, such as terpenoids, which are terpene derivatives including molecules that have undergone one or more steps of functionalization such as hydroxylations, isomerizations, oxido-reductions, dimethylation, or acylation, for example.

Within the context of this specification the word "comprises" is taken to mean "includes, among other things". It is not intended to be construed as "consists only of".

In a preferred embodiment, the plant of the present invention is transformed to comprise a structural gene comprising a nucleotide sequence encoding a prenyltransferase (PRT) targeted to the plastid of the plant.

According to another preferred embodiment, the plant of the present invention is transformed to comprise a structural gene comprising a nucleotide sequence encoding a terpene synthase (TS) targeted to the plastid of the plant.

The term "targeted to the plastids of the plant" refers to the fact that the PRT and/or the TS will be present in the plastids. These proteins may be targeted to the plastids by nuclear transformation with genes comprising plastid-targeting sequences resulting in gene products being actively transported into the plastids by the plant cell. Another possibility of targeting proteins to the plastids is by transforming the plastid genome directly, in case of which plastid-targeting sequences may no longer be necessary, for example. The plants of the present invention are preferably transformed to comprise genes encoding a PRT and a specific TS targeted to the plastids of the plant cell.

Preferably, the plants of the present invention express PRT and/or TS. Preferably, the plants over-express PRT and/or TS. Expression of PRT or TS is preferably determined by RNA extraction and quantitative RT-PCR analysis following the protocol given in the examples.

Prenyl transferases (PRT), also called polyprenyl diphosphate synthases or polyprenyl pyrophosphate synthases are enzymes that catalyse alkylation steps involving dimethylallyl diphosphate (DMAPP) and one or more IPP residues, for example farnesyl diphosphate (FPP), geranyl diphosphate (GPP), geranlygeranyl diphosphate (GGPP), or others. The term PRT also includes one or several distinct enzymes capable of catalysing one or a sequence of reactions leading to the polyprenyl diphosphate precursor for the various terpenoid families. Therefore, at least one nucleotide sequence encoding a PRT, for the purpose of the present invention, encompasses sequences encoding for polypeptides having quaternary structures comprising homo- and hetero mixtures of mono-, di-, tri-, tetra-, and ologomeric proteins. In particular, the PRT may be a monomer, a hetero- and/or a homodimer. The geranyl diphosphate synthase from oil glands of peppermint (*Mentha piperita*) may serve as an example for the complex genetic organisation of certain PRTs encompassed by the present invention, as this enzyme has been purified and was revealed to be a heterodimer, with both subunits required to produce GPP from IPP and DMAPP precursors.

Preferably, PRTs encompass enzymes classified under EC number EC 2.5.1, for example.

In a preferred embodiment, the at least one nucleotide sequence encoding a PRT encodes one or more proteins having the activity of a geranyl-diphosphate (GPP) synthase, and/or a farnesyl-diphosphate (FPP) synthase. GPP and FPP are the precursors for mono-, and sesquiterpenes, respectively.

Geranyl-diphosphate synthases (GDS), also called dimethyl-allyl-transtransferases, are examples for PRTs.

According to a preferred embodiment, the PRT is a farnesyl diphosphate synthase (FPS). FPSs are enzymes that catalyse, for example, the condensations of geranyl diphosphate (GPP) with IPP to give farnesyl diphosphate. Preferably, the FPS is capable of catalysing the sequential condensation of isopentenyl diphosphate (IPP) with the allylic diphosphates, dimethylallyl diphosphate (DMAPP), and then with the resultant geranyl diphosphate (GPP) to the ultimate product farnesyl diphosphate. Preferably, the PRT present in the transformed plant is isolated from a species different from the transformed plant. According to a preferred embodiment, the PRT is a non-plant PRT. Preferably, the PRT is an animal or fungal PRT, more preferably an animal PRT. Preferably, the PRT vertebrate, more preferably from a bird. Preferably, the PRT is a non-plant farnesyl diphosphate synthase.

For the purpose of the present invention, the transformed plant preferably comprises genes encoding a specific TS and the PRT capable of synthesising the direct precursor of the specific TS as indicated above. For example, a plastid targeted sesquiterpene synthase and a plastid targeted FPS. This is a particularly preferred embodiment of the present invention, because it utilises the MEP pathway for producing sesquiterpenes, which has previously not been demonstrated. As another example, the plants is transformed to comprises genes encoding a plastid targeted GDS and a plastid targeted monoterpene synthase.

A large number of nucleotide sequences encoding PRTs isolated from various organisms are readily available to the skilled person and can be downloaded from public databases. It is an important advantage of the present invention that the nucleotide sequence of any PRTs capable of synthesising the precursor of any corresponding TS may be interchangeably employed in the plants of the present invention.

Publicly available databases suitable for obtaining nucleotide sequences encoding PRTs or TS are, for example, the database of the European Bioinformatics Institute, (http://www.ebi.ac.uk/swissprot/index.html), the EXPASY database (http://www.expasy.org/enzyme/), the NCBI database (http://www.ncbi.nlm.nih.gov) and many others. For the mere purpose of illustrating the many possibilities of FPSs available to the skilled person that could be used for the purpose of the present invention, one could cite a geranyl diphosphate synthase isolated from *Ips pini* (NCBI Accession number (AN): AY 953508.1), a farnesyl diphosphate synthase isolated from *Vibrio fischeri* (NCBI AN: YP 203660), and an avian farnesyl diphosphate synthase reported by Tarshis et al (1994). Of course, any other PRT could be selected from any database.

TS are enzymes that catalyse the formation of a mono- or sesquiterpene from a given precursor compound. An important advantage of the present invention is the exchangeability of the specific terpene synthase. Depending on the particular sesquiterpene that the skilled person is interested in, any corresponding TS can be selected and the nucleotide sequence encoding it can be used for transforming the plant of the invention.

The term "specific" or "selected" terpene, TS or PRT refers to a TS or PRT at the choice of the skilled person. Depending on the "specific" terpene of interest, the nucleotide sequences encoding the PRT and the TS that are capable of synthesising the respective precursor and the terpene of interest are used to prepare the transformed plants. Preferably, the nucleotide sequence encoding the specific TS or PRT, which may be any TS or PRT, is readily available or can be isolated by the skilled person. For example, a "specific" terpene may be a compound having desirable properties as a fragrance, a flavor, a medicinal compound, a vitamin, a insect control agent, a plant control agent, just to mention a few, and may be selected by the skilled person due to any of these properties. The present invention then provides a versatile system that allows for the production or accumulation of the very terpene of interest in plants.

Preferably, the specific TS is a terpene synthase which utilizes any of GPP and/or FPP as an intermediate or precursor up-stream in the terpene biosynthetic pathway in which it naturally occurs. In this case, the carbon flux is more extensively directed towards the accumulation of the specific terpene synthetised by the TS. For example, the TS has farnesyl diphosphate as its direct substrate.

In an embodiment, the TS of the present invention is preferably selected from the group consisting of a monoterpene and a sesquiterpene synthase. Any terpene synthase may be used for the purpose of the present invention. Examples of monoterpene synthases with available sequences are the limonene synthase (LS), (Ohara et al, 2003), S-linalool synthase (LIS), (Lucker et al 2001).

Genes or nucleotide sequences encoding terpene synthases isolated from various organisms can readily be downloaded from publicly accessible databases (see above for PRTs) and are also disclosed in the literature.

According to an embodiment, the TS is a sesquiterpene synthase. Any sesquiterpene synthase is suitable for the purpose of the present invention, as these enzymes often catalyse a series of reactions leading to a specific sesquiterpene.

Amongst the large number of known sesquiterpenes, one can differentiate different classes according to the intermediate carbocation of the diphosphate precursor before obtention of the final sesquiterpene. For example, TS include enzymes forming the trans-humulyl cation to synthesise β-caryophyllene and α-humulene, amongst others. Other TSs form the intermediate E,E-germacradienyl cation to obtain germacrene A, B, C, D, valencene, aristolochene, vetiapinadiene, for example. Of course many other TS are known and can be employed for the purpose of the present invention.

In a preferred embodiment, the TS is a sesquiterpene synthase selected from the group consisting of a patchoulol synthase, valencene synthase, and a cubebol synthase. Alternatively, the TS is a γ-curcumene, (−)-germacrene D, (+)-germacrene D, bicyclo-germacrene, cubebol and/or 6-cadiene synthase. Genes encoding such synthases have been disclosed in the international applications PCT/IB/2004/003836 and WO 2004/031376.

The above examples represent only very few, arbitrarily selected examples of the large number of published sequences suitable for the purpose of providing a sequence encoding a PRT or a TS for the present invention. Accordingly, these few examples of different TSs and PRTs suitably illustrate the wide applicability of the terpene production platform of the present invention, according to which a suitable way for producing any terpene at the discretion of the skilled person is provided.

Preferably, the structural genes in the plant of the present invention encode a functional FPS and a functional TS.

The gene encoding the PRT and/or the TS may be isolated from the plant to be transformed itself. In this case, the transformation of the plant results in additional copies of genes encoding the PRT and/or TS in the transformed plant. Preferably, however, the FPS and/or the TS are heterologously expressed enzymes in the transformed plant.

Preferably, the genes comprising a nucleotide sequence encoding a TS and/or a PRT are transgenes.

In a preferred embodiment, the transformed plant of the present invention accumulates at least 1.5 as much of a specific terpene that can be synthesized by the TS if compared to a native, untransformed plant. Preferably, the transformed plant accumulates at least twice, three times, more preferably at least four times and most preferably at least 6 times as much of the specific terpene.

According to another embodiment of the invention, the transformed plant accumulates at least 1000 ng (nanograms)/per g of fresh leaf of a specific terpene that can be synthesized by the TS. Preferably, the transformed plant accumulates at least 1000 ng, more preferably at least 4000 ng, even more preferably at least 5000 ng, still more preferably at least 7000 ng of the specific terpene that can be synthesized by the recombinant TS present in the transformed plant. According to a preferred embodiment, the transformed plant accumulates at least 10000 ng/g of a terpene, preferably a sesquiterpene, that can be synthesized by the TS. Preferably, the transformed plant accumulates at least 13,000 ng, more preferably at least 20,000 ng, even more preferably at least 25,000 ng and most preferably more than 30,000 ng of the specific terpene per g of fresh leaf. The quantity of the specific terpene may also be expressed in weight of dry matter. In this case, dry matter plant materials, and in particular leaves, corresponds to about 10% of the values for fresh weight. Accordingly, at least 10, 40, 50, 70, 100, 130, 200, 250, 300 μg terpene per g of dry leaf are accumulated.

In case the native, untransformed plant already produces the specific terpene, the above values valid for the transformed plant are added to the amount of the specific terpene natively present in the untransformed plant.

For determination of the content of the specific terpene in the plant of the present invention, any plant organ producing or accumulating terpenes may be taken as a reference. Preferably, green leaves having the same age are taken from the transformed and non-transformed plant, respectively, for comparison. In general, adult leaves are taken. The analysis is preferably conducted according to the protocol "Terpene analysis" outlined in the examples. Preferably, fresh leaves are analysed directly after cutting from the plant. Leaves may be frozen after harvesting and be analysed in the frozen state.

According to a preferred embodiment, the transformed plant according to the invention is the transformed *Nicotiana tabacum*. Seeds of the plant of the present invention have been deposited at the ATCC, 10801 University Blvd, Manassas, Va. 20110-2209, USA, under the depositor's sample references "tpPTS+tpFPS-4" and "pBtpPTS+tpFPS-4" and the Patent Deposit Designations ATCC PTA-6659 and PTA-6660, respectively.

Preferably, the transformed plants may comprise knock-out, deletion or other forms of deleterious mutations in selected wild-type genes participating to the terpene biosynthetic pathways suitable to deviate the carbon flux away from the TS of the present invention. For example, the plants of the present invention may have one or more non-functional genes downstream the FPP, GPP and/or GGPP synthases encoding genes leading to the synthesis of sterols, polyprenoids, phytols and carotenoids. In this way, carbon-flux may more efficiently be directed towards the synthesis of the specific terpene.

The present invention provides for methods of altering and/or increasing the content of specific terpenes in a plant, said methods including a step of transforming plant material with at least one DNA construct comprising structural genes targeted to the plastids of the plant.

Generally, any method for transforming plants with the structural genes of the present invention may be employed. For example, plant cells that have been stripped of their protective cell walls take up pure DNA when treated with certain membrane-active agents or with electroporation. DNA can also be microinjected into target plant cells using very thin glass needles. A recently developed method of plant transformation, biolistics, involves accelerating very small particles of tungsten or gold coated with DNA into cells using an electrostatic pulse, air pressure, or gunpowder percussion.

For example, the structural genes may be directly engineered into the plastid, preferably along with a suitable plastid expression vector. Suitable methods for transforming the plastid genome of plants are disclosed in Lutz K. A., Corneille S, Azhagiri A. K., Svab Z., Maliga P. (2004) A novel approach to plastid transformation utilizes the phiC31 phage integrase. Plant journal 37: 906-913.

Accordingly, the present invention provides, in a preferred embodiment, plants in which the structural genes encoding a PRT and a TS are present within the plastid genome and are operatively linked to a plastid expression promoter.

Alternatively, the gene products may be targeted to the plastids by transforming plant material on the level of its nuclear DNA. Accordingly, the invention provides, in a preferred embodiment, plants in which the structural genes comprising nucleotide sequences encoding a PRT and a TS are nuclear genes and comprise, linked to the nucleotide sequence encoding a PRT and/or a TS, a plastid targeting sequence.

According to a preferred embodiment of the invention, the terpene, preferably the sesquiterpene, is, at least in part biosynthesised via the MEP pathway. Preferably, at least 30% of the terpene that can be synthesised by the terpene synthase is bio-synthesised via the MEP pathway. Preferably, at least 50%, more preferably at least 60% and most preferably at least 80% are obtained through the MEP pathway. The MEP pathway generally uses glyceraldehydes and pyruvate as substrates for synthesising isopentenyl-diphsophate. This pathway is characterized by the intermediate 2-C-methyl-D-erythritol-4-phosphate. It generally takes place in the plastids. A further pathway for IPP, the MVA pathway, generally takes place in the cytosol.

In IPP synthesised by the MEP pathway, carbons of the IPP are differently arranged than if IPP was synthesised through the MEV pathway, resulting in a different arrangement of carbon atoms in the resulting terpene. The different way of arranging carbons in the MEP and the MVA pathways can be utilised for identifying the bio-synthetic origin of a terpene in labelling experiments. For example, incorporation of [1-$^{13}$C]-glucose by the MEP pathway results in IPP having 2 $^{13}$C-labelled carbon atoms, whereas 3 such atoms should be present in IPP resulting from the MVA pathway.

The present inventors have obtained good results with the *Agrobacterium tumefaciens*-mediated transformation. Preferably, plasmid constructs (vectors) comprising at least one of the structural genes of the present invention, flanked by nucleotide sequences that allow integration of the structural genes into the plant nuclear chromosome DNA are used.

In an aspect, the present invention provides a vector comprising a nucleotide sequence encoding a PRT and/or a TS, or a fusion protein of a PRT and a TS, said structural gene further comprising a plastid targeting sequence up-stream or downstream the sequence encoding a PRT, TS or fusion protein. In other words, the vector may comprise only one or both of a nucleotide sequence encoding a PRT and a TS, or a nucleotide sequence encoding a fusion protein of both.

Suitable plastid targeting sequences include sequences encoding a plastid or chloroplast transit peptide. Plastid targeting sequences are known to the skilled person and can be linked in frame to the nucleotide sequence encoding the PRT and/or the TS. One out of many possible examples of available plastid targeting sequences are the *Arabidopsis thaliana* RUBisCO small unit gene (GenBank accession no. NM123102).

Preferably, the plastid targeting sequence is situated at the N-terminal end of the structural gene encoding a PRT and/or TS.

Preferably, the vector further comprises promoter and terminator sequences, preferably up-stream and downstream the nucleotide sequence including the plastid targeting sequence and the structural gene for the PRT and/or TS, respectively. Preferably, the vector comprises strong constitutive promoters. Examples for promoters are the MOS and NOS promoter. Preferably, the promoters are selected to be independent from control and/or feed back regulation mechanisms of the untransformed host plant. Preferably, the recombinant PRT and TS have up-stream promoter sequences. More preferably, they have each different promoter sequences.

Optionally, the vector may further comprise tags suitable for antibody binding, such as His-tags and/or myc tags.

Preferably, the vector of the present invention further comprises a marker suitable for selecting transformed plants. For example, the vector may comprise genes conferring a hygromycin or a kanamycin resistance, or any other kind of marker suitable to select for successfully transformed plants.

Preferably, the vector of the present invention further comprises a left and a right border region, flanking the PRT and/or TS including optional promoter, terminator, tagging and/or plastid targeting sequences, as well as plant resistance markers, in order to facilitate integration of the structural genes into the plant nuclear genome.

Accordingly, the vector of the present invention preferably comprises structural genes encoding a PRT and/or a TS, linked to at least one plastid targeting sequence, and a marker for selection of transformed plants, flanked by left and right border regions facilitating insertion into the plant genome.

Preferably, the vector further comprises, outside the left and right border region, a marker for selecting positive bacterial transformants used to clone bacteria comprising the vector or used for transformation of plants (*A. tumefaciens*).

Transformation of plant material with a DNA construct comprising structural genes targeted to the plastids of the plant may be performed by standard methods, see Schardl et al, Gene (1987) δ: 61: 1-11; Berger et al, Proc Natl Acad Sci USA (1989) 86: 8402-8406; and Horsch et al, Science (1985) 27: 1229-1231, the latter method describing the "leaf disk method", which is particularly suitable for transforming *Nicotiana tabacum*.

The methods of the present invention further comprise the step of regenerating the transformed plant from the transformed plant material. Methods for regenerating entire plants from transformed plant material are routinely applied by the skilled person. For example, the method disclosed by Horsch et al (1985) may be employed. In general, segments of leaves comprising transformed cells may be grown in selective media until callus and regenerated plant shoots are evident. Shoots of 1-3 cm in size may be transferred to T-Media (Schardl, 1987) containing antibiotics to stimulate root development. Once root systems are established, the plantlets may be transferred to commercially available potting soil and propagated in a greenhouse.

The present invention further comprises a method for altering the content of specific terpenes produced in a plant, the method comprising the steps of transforming a first plant material with a nucleic acid encoding PRT, transforming a second plant material with a nucleic acid encoding a TS, regenerating a first and a second plant from the first and the second transformed plant material, respectively, crossing the first and the second plant, and, selecting from progeny obtained by the crossing for plants over-expressing both, the recombinant PRT and the recombinant TS.

The above method is a variant method for obtaining the transformed plant of the invention, in that different plant material is separately transformed with a structural gene encoding a PRT or a TS, and transformed plants are regenerated comprising only one of the two recombinant genes.

In a following step, sexually derived progeny is obtained from crossing plants containing recombinant PRT DNA with plants comprising recombinant TS DNA. Preferably, crossing refers to genetic, also called Mendelian crossing. This may typically be done by cross-pollinating. Among the progeny, individuals expressing both, the recombinant PRT as well as the TS are selected.

The present invention further provides a method for producing a specific terpene, the method comprising the step of isolating the terpene from the transformed plant of the invention. The transformed plant may be cultivated and harvested, preferably in sufficiently high amount to render the process economically favourable. The specific terpenes of the invention may be isolated by any method used in the art including but not limited to chromatography, for example gas chromatography (GC) extraction and distillation.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, exemplary methods and materials are described for illustrative purposes. All publications mentioned in this application are incorporated by reference to disclose and describe the methods and/or materials in connection with which the publications are cited.

EXAMPLES

The following examples are intended to illustrate the invention without limiting the scope as a result. Methods and protocols of the examples are generally performed following standard protocols supplied by the manufacturer of specific materials or kits, or by following well-established protocols defined by Sambrook et al (1989) and Ausubel et al. (1987).

The attached sequence listings include nucleic acid sequences encoding sesquiterpene synthases and an avian farnesyl diphosphate synthase, coupled to transit peptide sequences.

The nucleotide sequence encoding a patchoulol synthase (bp187-bp1845) linked via a linker sequence to a plastid targeting sequence (bpp1-bp171) is named tpPTS (SEQ. ID. NO:1).

The nucleotide sequence encoding an avian farnesyl diphosphate synthase synthase (bp211-bp1314) linked via a linker sequence to a plastid targeting sequence (bp1-bp171) is named tpFPS (SEQ. ID. NO:2).

The nucleotide sequence encoding a fusion protein in which a PTS encoding region (bp1321-bp2979) is fused to an avian FPS-encoding region (bp211-bp1311) avian farnesyl diphosphate synthase and further linked via a linker sequence to a plastid targeting sequence (bp1-bp171) is named tpFPS-PTS (SEQ. ID. NO:3)

The nucleotide sequence encoding a amorpha-4,11-diene synthase (bp181-bp1821) linked via a linker sequence to a plastid targeting sequence (bp1-bp171) is named tpADS (SEQ. ID. NO:4).

Primers used in the PCR reactions described in the examples are listed under SEQ. ID. NO. 5-70.

Peptide fragments used for preparing antibodies for western blotting are listed under SEQ. ID. NO. 71-78.

For some method or protocol steps, reference is made to the literature, which is listed further below in more detail.

The plant material used to produce plants having their nuclear DNA transformed are *Nicotiana tabacum* L. cv. Xanthi. Plants having their plastidic DNA transformed are *Nicotiana tobacco* LA63.

Examples 1-5

Construction of Recombination and Plant Transformation Vectors

The hygromycin selection marker (Hajdukiewicz et al., 1994) was chosen for creating a selection marker for transformed plants. New vectors were engineered with appropriate recombination cloning sites as described by Hartley et al. (2000).

Example 1

Figure 8:
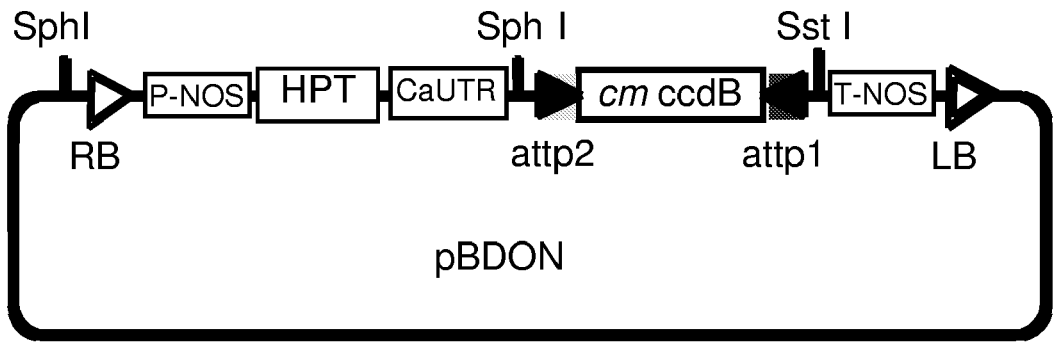
FIG. 8 shows the organisation of a vector ("pBDON") suitable for A. tumefaciens-mediated transformation of plants, in which the region between the attp2 and the attp1 sequence (cm ccdB) may in vitro and site-specifically be recombined to harbour a TS, and/or PRT targeted to the plastid of the plant. The vector comprises border regions for transformation of plants, promoters, terminators, and the attp1/2 recombination sequences, as discussed in further detail in the examples.
Figure 11:
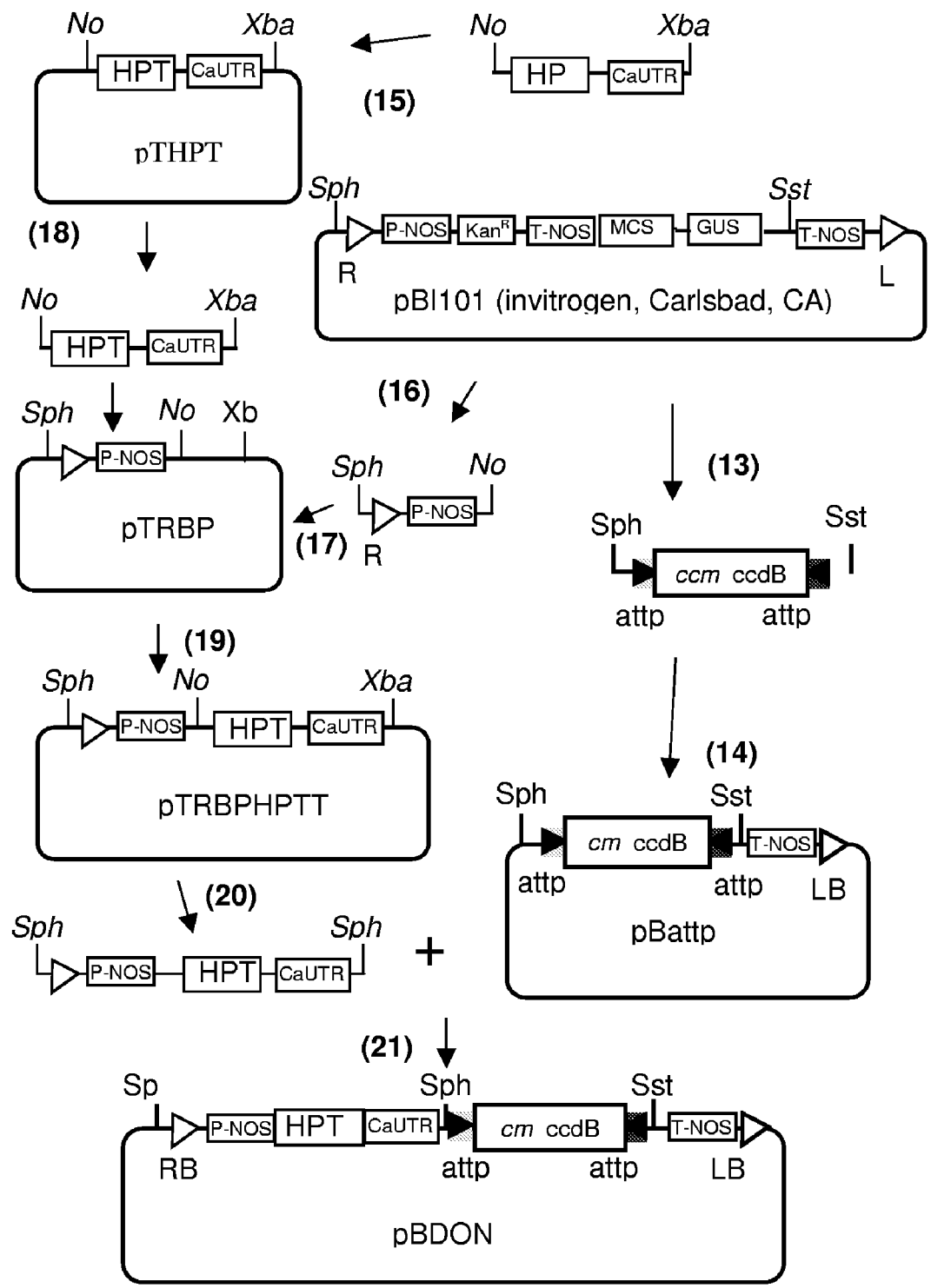
FIG. 11 schematically shows the construction of pBDON vector (FIG. 8).

Development of the pBDON Vector (FIGS. 8 and 11)

The pBI101 vector (Invitrogen, Carlsbad, Calif.) was digested with the restriction enzymes Sph1 and Sst1 and the DNA fragment corresponding to the plasmid vector (not including the RB border and NPTII gene cassette) was isolated by agarose gel purification (Sambrook et al., 1989) (13). In parallel, an attp recombination cassette including the ccdb gene and chloroamphenical resistance gene was amplified from the pDON221 vector (Invitrogen, Carlsbad, Calif.) using standard PCR conditions with primers Attp1-SstI-FW and Attp2-SphI-R$^V$. The PCR amplified DNA fragment was restricted with the Sph1/Sst1 enzymes, gel purified and ligated into the corresponding sites of the similarly digested pBI101 vector described above to yield the intermediate pBattp vector (14).

A hygromycin gene cassette was prepared in a 2-step process. First, the hygromycin gene and CaUTR (termination sequence) was PCR amplified from the pCAMBIA1301 (Cambia, Can berra, AU) vector using the PCR primers HPT-NotI-FD and HPT-Xba1-RV, and T/A cloned (Taq-Amplified PCR products directly from the PCR reaction mix) into the pT7Blue vector (Novagen, Madison, Wis.) to yield pTHPT (15). The right border (RB) and the NOS-promoter (P-NOS) regions were amplified from pBI101 using the PCR primers TB-SphI-FD and TB-NotI-RV (16), then T/A cloned into the pT7Blue vector giving rise to vector pTRBP (17). The hygromycin resistance gene cassette was released from vector pTHPT via digestion with NotI/XbaI (18), and cloned into the similarly digested pTRBP vector, resulting in vector pTRB-PHPTT (19). The NOS promoter-hygromycin-CaUTR cassette was then amplified from this vector using the primers TB-SphI-FD and HPT-SphI-R (20). The amplified product was digested with Sph1 and ligated into the corresponding site of pBattp, yielding the pBDON vector (21).

The pBDON Ti-vector (FIG. 8) contains an NPTII selection marker outside the T-DNA region for selection in bacteria and the hygromycin gene (HPT) for plant transformation selection. The embedded attp cassette hence provides for the easy insertion of target gene constructs flanked with attB sites into the pBDON vector.

Figure 12:
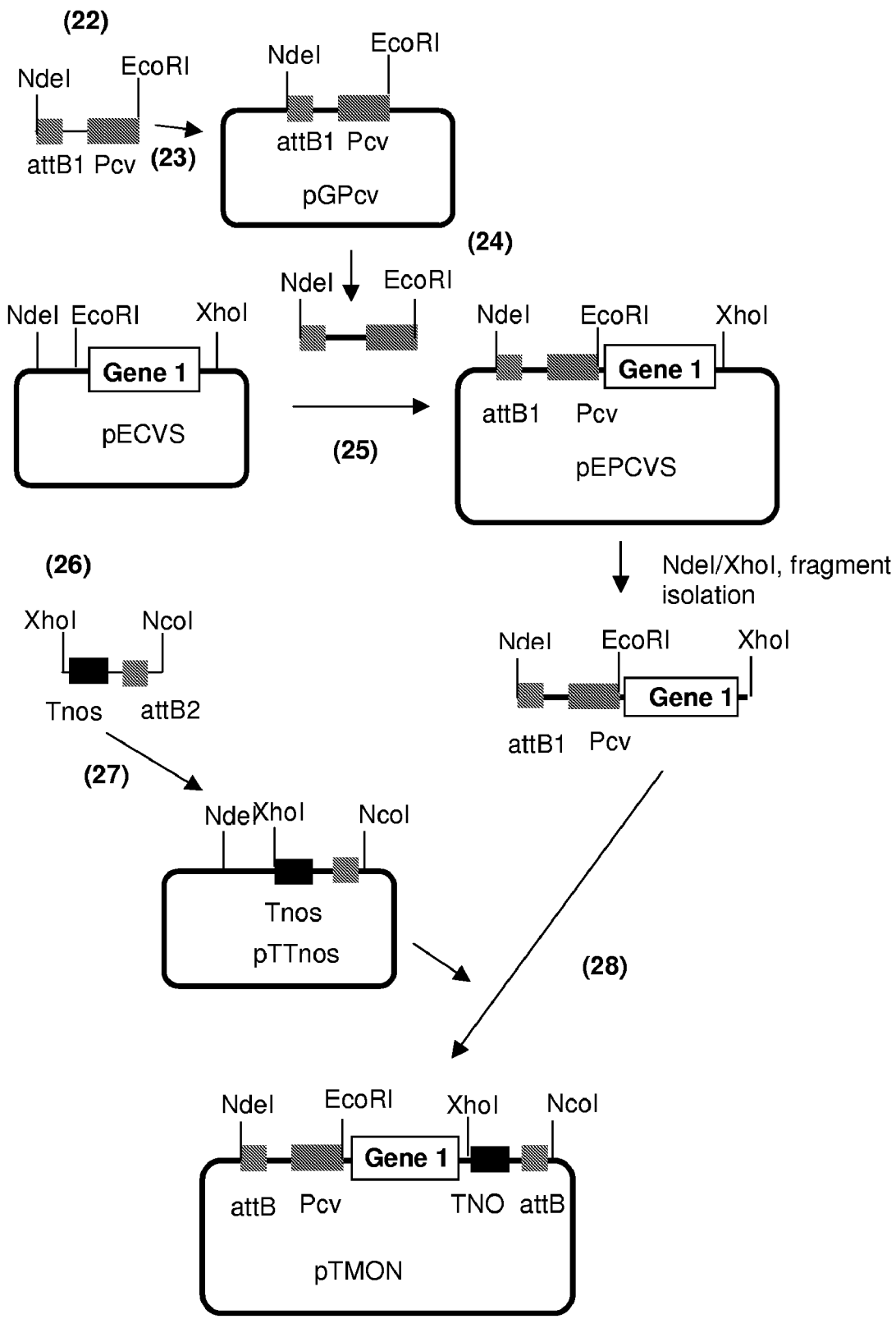
FIG. 12 schematically shows the construction of pTMON helper vector (FIG. 9 A).

Two different attB help vectors with attB sites (FIGS. 9 A and B) were constructed following the protocol given in FIGS. 12 and 13. One for single gene insertion (pTMON, FIG. 9 A) and the other for two target gene insertions into the pBDON vector (pTDUAL, FIG. 9 B).

Example 2

Generation of the pTMON Vector (FIGS. 9A and 12)

The pTMON vector was constructed by first amplifying the cassaya mosaic virus promoter from a modified pBI101 vector with a forward PCR primer containing a Nde1 restriction site and an attB1 sequence embedded into the primer CSMV-ATTB1-SGFI-FD, and the reverse primer CSMV-ECORI-RV containing an EcoR1 site (22). The PCR fragment was T/A cloned into the pGem-Teasy vector (Promega, Madison, Wis.) (23), then re-isolated as a Nde1/EcoR1 digestion product (24). The isolated digestion product was ligated into the corresponding restriction sites of the pECVS vector, a pET28a derivative harboring a terpene synthase gene ("Gene 1"), to generate pEPCVS (25).

Figure 9:
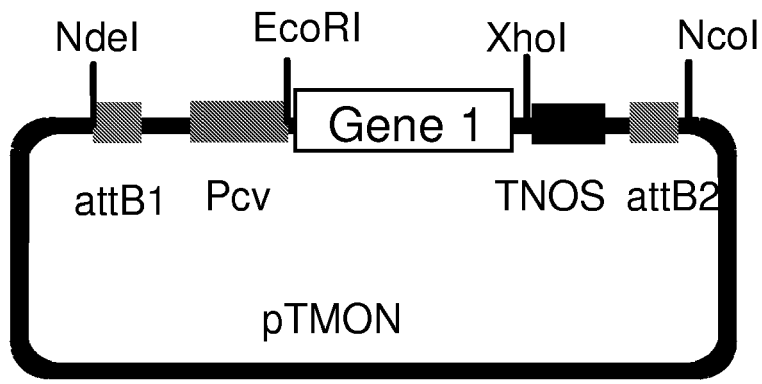
FIGS. 9 A and 9 B show helper vectors ("pTMON" and "pTDUAL") comprising, between the attp2 and the attp1 sequence, one or two structural genes, respectively, to be inserted by site-specific recombination into the vector pBDON of FIG. 6. Part A shows the helper vector suitable to insert one gene at a time into the pBDON vector, while part B shows the helper vector suitable to insert two genes at a time into pBDON. The vectors comprises promotor, terminator, attp1/2 recombination and place-holder sequences CVS, HPO, as discussed in further detail in the examples.
Figure 9:
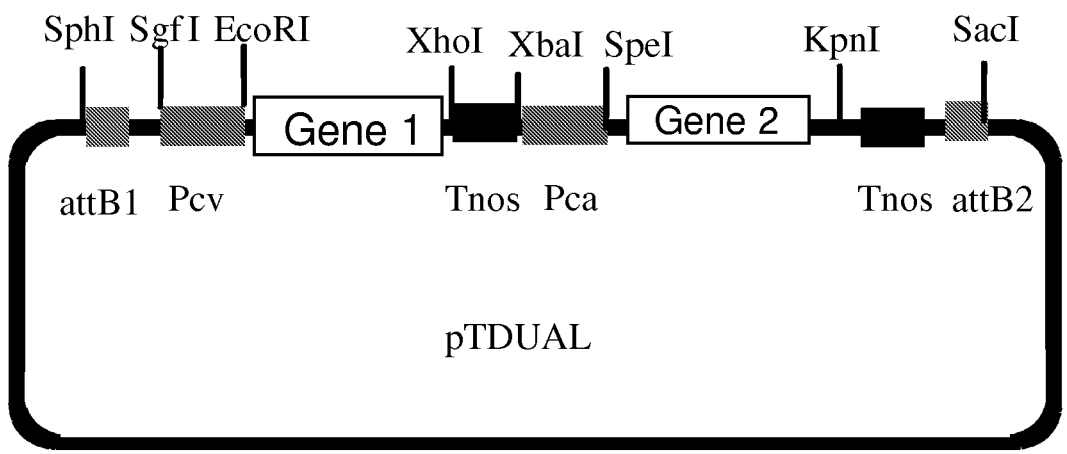

In parallel, the NOS terminator (TNOS) sequence of pBI101 was amplified with the forward primer Tnos-XhoI-FW and the reverse primer Tnos-attB2-RV (26), which incorporated an attB2 recombination site downstream of the TNOS sequence. The PCR fragment was T/A cloned into the pGEM-Teasy vector, yielding the pTTNOS vector (27). An Nde1/Xho1 digestion fragment of pEPCVS was subsequently ligated into the corresponding sites of pTTNOS to generate pTMON (28) (FIG. 9 A).

The pTMON vector was constructed for insertion of a single target gene behind a cassaya mosiac virus promoter (Pcv) (Frey et al. 2001) and followed by the Nos terminator sequence.

A plastid targeting sequence was engineered into the pTMON vector. Accordingly, the plastid targeting sequence of the *Arabidopsis* small subunit RUBP carboxylase/oxygenase gene (GenBank accession NM123202) was amplified using the primers TP-ASCF and TP-ASCR, digested with AscI, and ligated into the corresponding restriction site of the mutated pTMON vector.

Example 3

Generation of the pTDUAL Vector (FIGS. 9 B and 11)

The pTDUAL vector was constructed in a multi-step process (FIG. 13, part I and II). First, the cauliflower mosaic virus promoter (Benfy et al. 1990) was amplified from the pBI121 vector (Invitrogen) using the primers PCaMV-XbaI-FW and PCaMV-SpeI-RV (29), and T/A cloned into the pT7Blue vector (30). The promoter element was subsequently released from this vector by digestion with Xba1 and Spe1 (31). In parallel, another terpene synthase gene ("Gene 2") was amplified with the primers 7120D-SpeI-FW and 7120D-KpnI-RV, followed by digestion with Spe1/Kpn1 and ligation into the corresponding site of a pT7Blue vector and yielding pTHPO (32). pTHPO was then digested with Xba1/Spe1 and the CaMV promoter fragment similarly released from pTPCa were ligated together to give pTPHPO (33).

In parallel to building pTPHPO, the NOS terminator sequence was amplified from the pGTNOS vector with primers Tnos-KpnI-FW and Tnos-attB2-RV3, T/A cloned into the pGem-Teasy vector (34) followed by subsequent re-isolation of the fragment by digestion of the pGTNOSK plasmid with Kpn1 and Sac1 (25). This fragment was then cloned into the corresponding restriction sites of pTPHPO to yield pTPH-POT (36) (part I of FIG. 11).

In the final steps of constructing the pTDUAL vector, a fragment of the pTMON vector spanning from the attB1 site to the nos-terminator sequence downstream of the inserted terpene synthase gene was amplified using standard PCR conditions (37). The amplification product was obtained with primers CsMV-attB1-Sgf I-FD and TNOS-XbaI-RV, which also engineered terminal Sph1 and Xba1 sites onto the fragment. The PCR fragment was digested and ligated into the corresponding Sph1/Xba1 sites of the pT7Blue vector, generating pTPCVST (38). Finally, an Xba1 to Sac1 digestion fragment (39) from pTPHPOT was ligated into the corresponding sites of pTPCVST (40) to create the pTDUAL vector, which allows for the insertion of 2 gene sequences downstream of strong, constitutive expression promoters (FIG. 13 part II).

The pTDUAL vector (FIG. 9 B) was designed for the insertion of two genes into transgenic plants. Expression of the first gene is directed by the cassaya mosaic virus promoter (Frey et al. 2001), while expression of the second gene is directed by a cauliflower mosaic virus promoter (Benfey et al. 1990).

A plastid targeting sequence was engineered into the pTDUAL vectors as for the pTMON vector. In these cases, the plastid targeting sequence of the *Arabidopsis* small subunit RUBP carboxylase/oxygenase gene (GenBank accession NM123202) was amplified with the either the primer pair TP-SpeFW; TP-SpeRV, or TP-ASCF; TP-ASCR, then digested with Spe1 or Asc1, respectively, before ligating the targeting sequence into the corresponding sites of the pTDUAL vector.

Example 4

Figure 14:
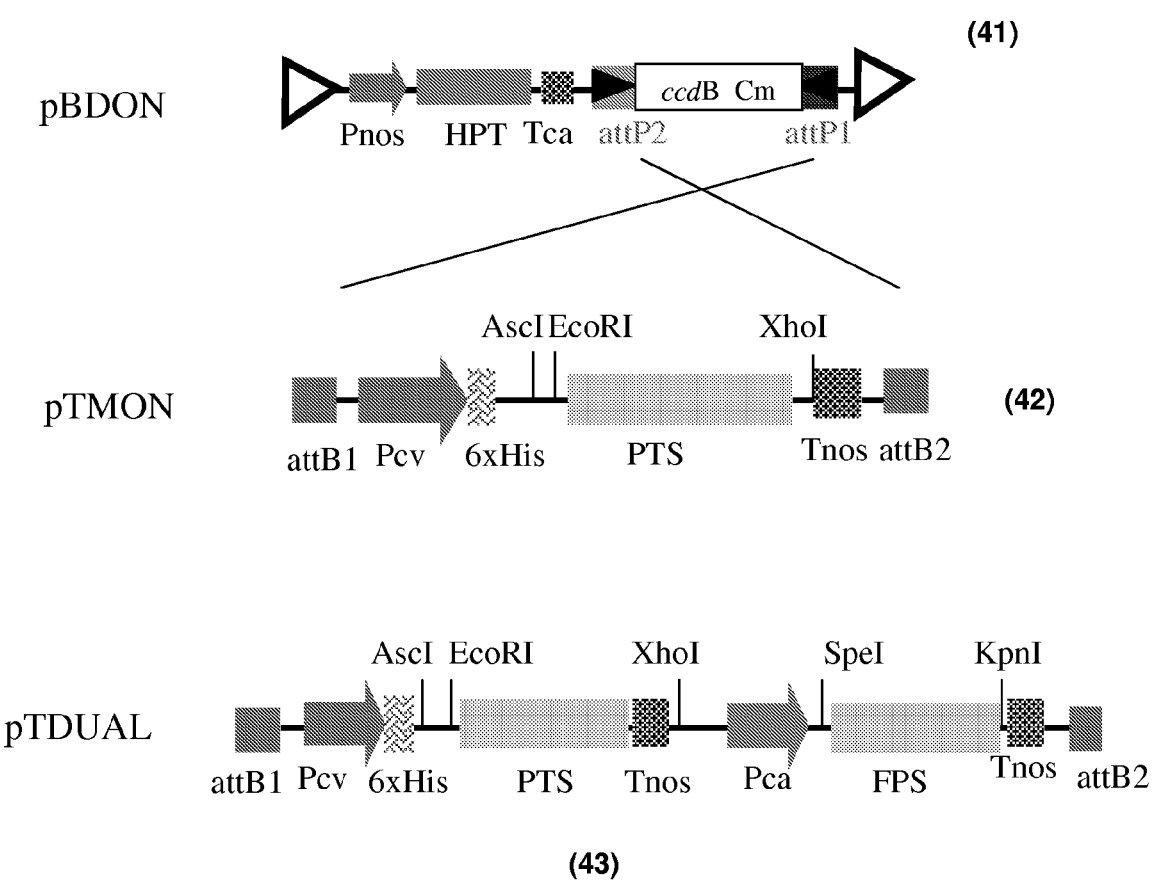
FIG. 14 shows the insertion of relevant fragments from helper vectors pTMON and pTDUAL (FIGS. 10 A and B) into the pBDON vector to obtain a family of suitable plant transformation vectors.
Figure 16:
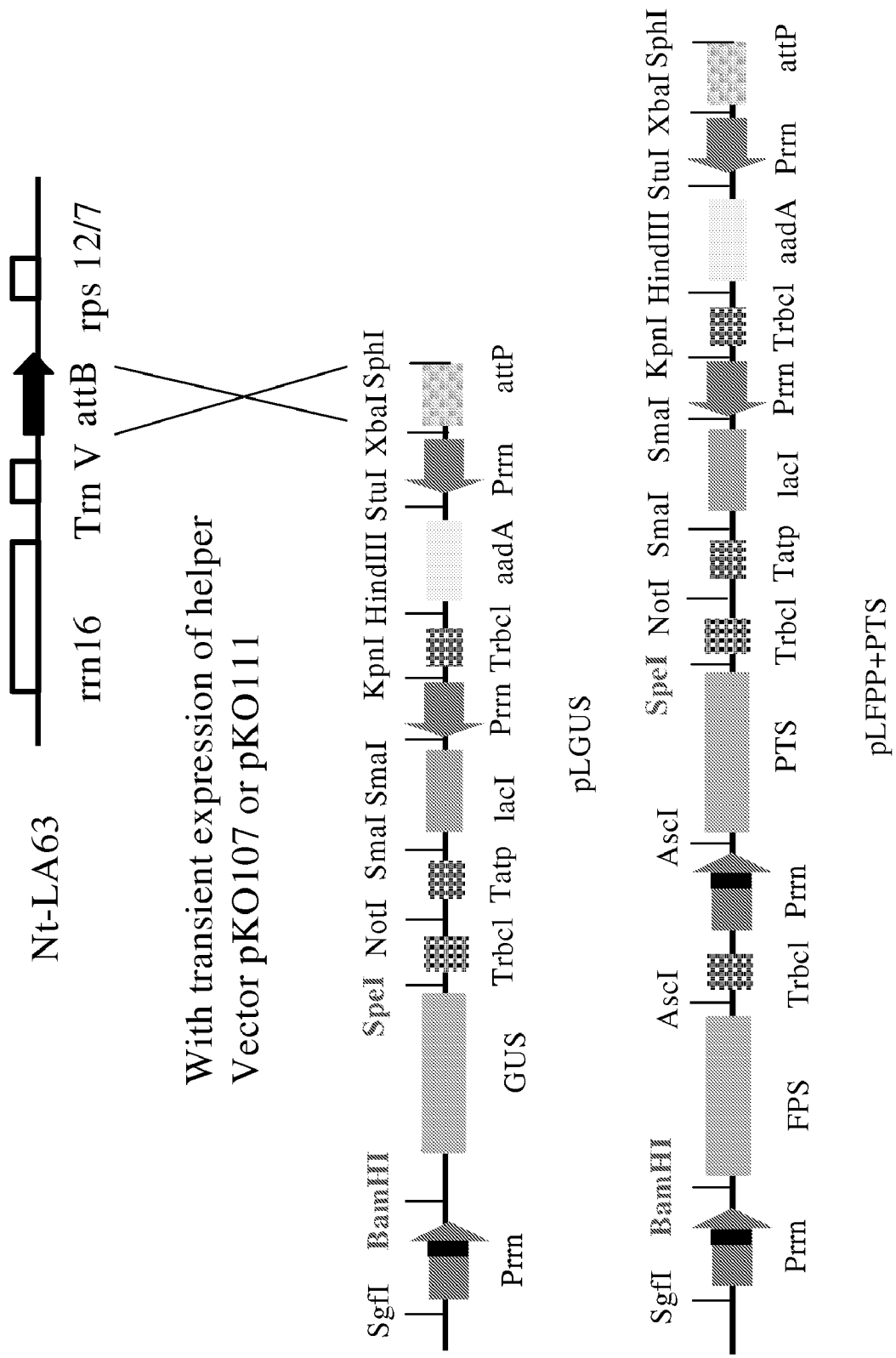
FIG. 16 shows the organisation of vectors pLGUS and pLFPP+PTS for transforming the plastid genome of plants with genes encoding GUS and FPS+PTS, respectively. Nt-LA63 is a *Nicotiana tabacum* strain of which the integration site for the transgenes, attB, is indicated.

Construction of the Patchoulol Synthase (PTS) and Patchoulol Synthase+Farnesyl Diphosphate Synthase (FPP) Over-Expression Vectors Generation of the PTS and PTS+FPS expression vectors were greatly facilitated by the appropriate recombination cloning sites associated with the pTMON, pTDUAL and pBDON vectors (FIG. 14). The PTS (WO 2004/031376) or FPS genes (Tarshis et al, 1994) and plastid targeting sequences were amplified with primer pairs PTS-AscF and PTS-XhoR, or FPP-SpeFW and FPP-KpnRV, respectively (41), digested with either Asc1/Xho1 or Spe1/Kpn1, then ligated into the corresponding sites of the pTMON (42) or pTDUAL (43) vectors. The FPS-PTS gene fusion was created by amplifying the FPS gene with primers FPS-AscF and FPS-AscR, digesting the resulting PCR fragment with Asc1 and ligating this fragment into the corresponding Asc1 site found 5' to the PTS gene in the pTMON and pTDUAL vectors. The resulting plasmids were then used to mobilize the corresponding PTS, PTS+FPS and FPS-PTS gene cassettes into the pBDON vector by standard recombination cloning (Hartley et al. 2000) generating a family of Ti-plasmid vectors (FIG. 8).

Example 5

Figure 10:
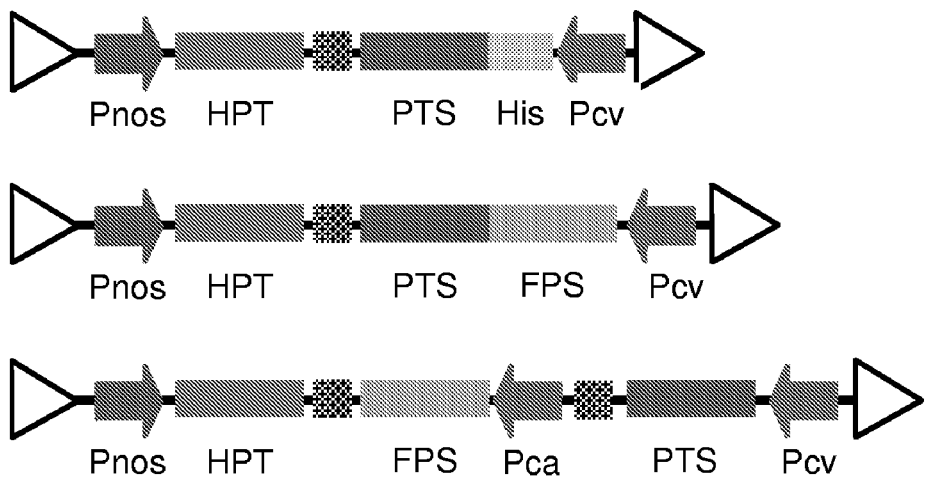
FIGS. 10 A and 10 B show the organisation of the T-DNA region of different plant transformation vectors. The HPT region provides hygromycin resistance, PTS encodes a terpene (patchoulol) synthase and FPS a farnesyl diphosphate synthase (a PRT). In some vectors, genes are flanked by a His-tag, or a plastid-targeting sequence (tp). The vector further comprises suitable promoter and terminator sequences.
Figure 10:
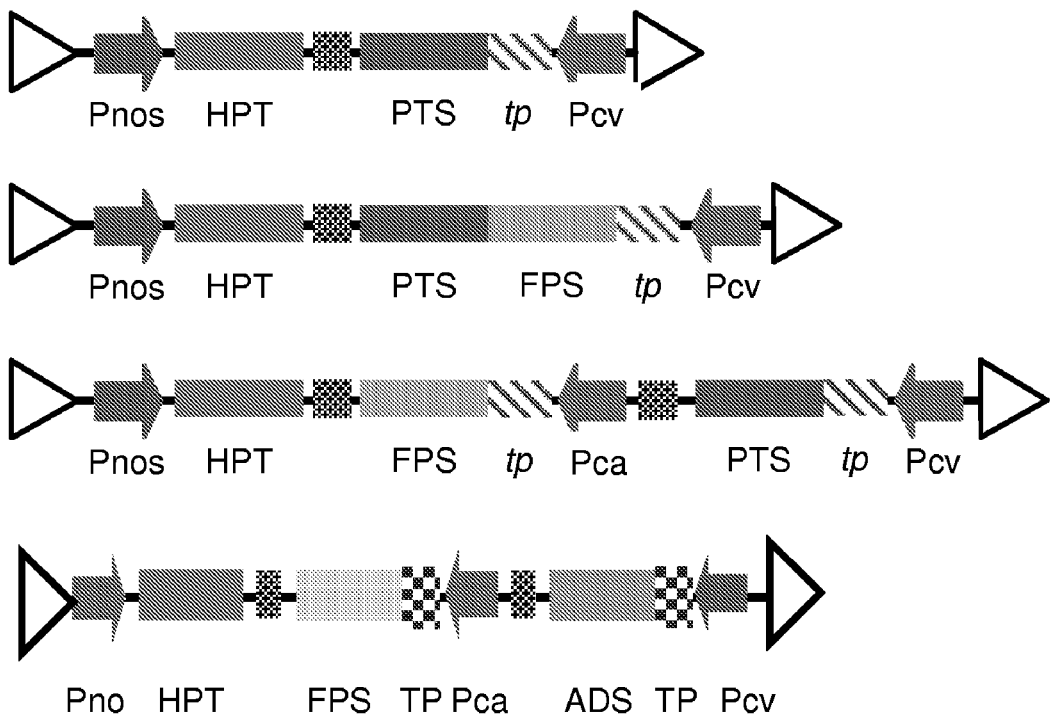

Construction of an Amorpha-4,11-diene Synthase (ADS) and Farnesyl Diphosphate Synthase (FPP) Over-Expression Vectors ADS cDNA (Genbank accession number AF138959) was kindly provided by Dr. Peter Brodelius, Kalmar University, Kalmar Sweden, was PCR amplified using the primers ADS-AscF and ADS-XhoR, and substitution cloned for the PTS gene in the pTDUAL vector also containing the tpFPS gene. DNA sequence encoding for the *Arabidopsis* transit peptide found associated with the small unit of ribulose-1,5-bisphosphate carboxylase (Rubis CO, GenBank accession no. NM23202) was PCR amplified with AscI restriction sites associated with the primers (primer sequences TP-ASCF and TP-ASCR), digested with the AscI restriction enzyme and introduced into the same restriction site 5' to the ADS cDNA gene, creating pTDUAL vector tpADS+tpFPS. The resulting plasmid was then used to mobilize the corresponding tpADS+tpFPS gene cassette into the pBDON vector by standard recombination cloning (Hartley et al., 2000) generating the corresponding Ti-plasmid vector (FIG. 10B, last construct).

Example 6

Plant Transformation and Regeneration

Individual pBDON vector constructs (FIGS. 10 A and 10 B) were transformed into *Agrobacterium tumefaciens* strain GV3850 by electroporation (Mersereau et al. 1990) and transformants selected for kanamycin resistance. Selected colonies were verified for the transgene constructs by limited DNA sequencing and subsequently grown in 50 mL of LB media containing 100 mg kanamycin/L. Overnight cultures having an $OD_{600}$ equal to 0.6-0.8 were concentrated by centrifugation, resuspended in a 30 mL of fresh LB medium (without antibiotic) and used for inoculation of leaf explants as described previous (Chappell et al., 1995; Horsch et al, 1985). In brief, leaves from plants grown under sterile conditions were placed into the *Agrobacterium* cultures, cut into approximate 1 cm segments, and the leaf segments plated on non-selective media plates (Murashige and Skoog, 1962). After 3 days, the leaf explants were transferred to media plates containing 15 μg/mL hygromycin (Invitrogen, Carlsbad, Calif.) and 500 μg/mL cefotaxime (Bioworld, Dublin, Ohio) and subsequently to the same selection media weekly until callus and re-generated plant shoots were evident.

Shoots of 1-3 cm in size were then transferred to T-media (Murashige and Skoog, 1962) (containing the same antibiotics) to stimulate root development. Once root systems were established, the plantlets were transferred to commercially available potting soil and propagated in a greenhouse.

Example 7

Terpene Analysis

Sesquiterpenes extracted from leaf material of transformed plants obtained in Example 6 were identified and quantified by GC-MS analysis. Frozen leaf samples of 250-500 mg were ground in liquid nitrogen, then extracted with 3 mL of a hexane:ethyl acetate mixture (v/v 85:15) containing 200 ng of $\alpha$-cedrene as an external internal standard. The extract was partially purified by running the sample over a silica column eluted with the same 85:15 mixture of ethyl acetate:hexane. The eluate was concentrated under a stream of nitrogen to 30 $\mu$L before analyzing 1 $\mu$L aliquots by GC-MS (Takahashi S, 2005). Samples were injected onto a Trace GC-MS (ThermoFinnigan, Somerset, N.J.) equipped with a Restec Rtx-5 capillary column (30 m×0.32 mm, 0.25 $\mu$m phase thickness) operated in the splitless mode with an injector temperature of 250° C. and an initial oven temperature of 70° C. for 1 min, followed by a 4° C. per min gradient to 230° C. Mass spectra were recorded at 70 eV, scanning from 35 to 300 atomic mass units, and compared to library standards (NIST library) and authentic standards for verification.

FIG. 1 shows the results of terpene analysis of a control tobacco line (WT) and one transformed with a tpPTS+tpFPS gene construct for sesquiterpene content. In FIG. 1, a total ion chromatogram for a transgenic line harboring the tpPTS+ tpFPS gene construct (A) is compared to that for a control plant (non-transformant) (B). Peaks were identified by comparison of their mass spectra to available standards or by spectral matches available in the NIST library. For example, the MS for peak 12 (C) is compared to the MS for authentic patchoulol (D). Other peak identifications: 1-$\beta$-patchoulene; 2-$\beta$-elemene; 3-$\alpha$-cedrene (internal standard); 4-caryophyllene; 5-$\alpha$-guaiene; 6-unknown; 7-$\alpha$-patchoulene; 8-seychellene; 9-unknown, 10-$\delta$-guaiene; 11-globulol; and 12-patchoulol.

Figure 2:
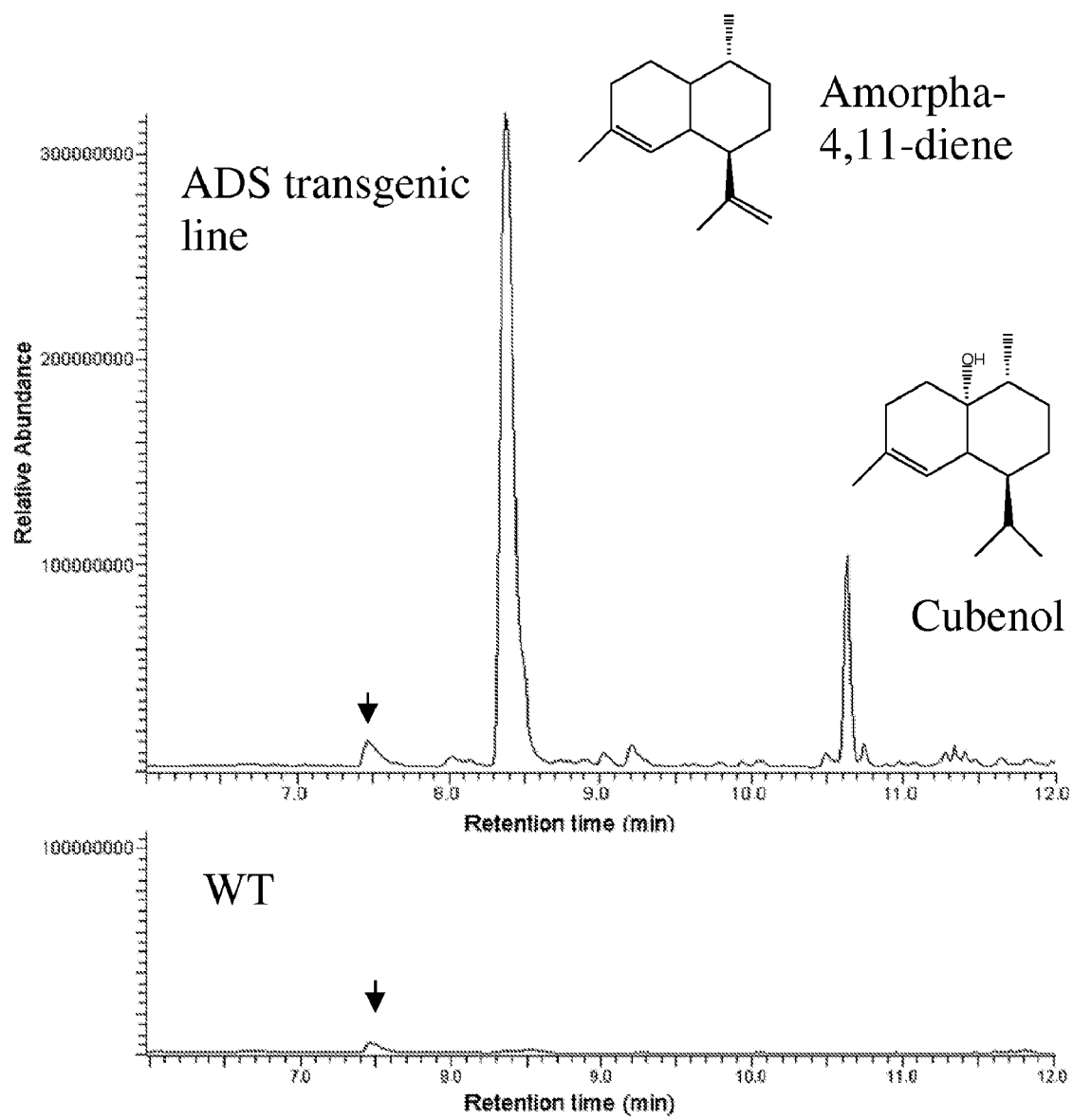
FIG. 2 shows GC-MS analysis of a control tobacco line (WT) and one transformed with a construct comprising plastid targeted genes encoding another sesquiterpene (amorpha-4,11-diene) synthase and a farnesyl diphosphate synthase (tpADS+tpFPS). The main peek shows accumulation of amorpha-4,11-diene in transformed plants.

FIG. 2 shows the results of terpene analysis of a control tobacco line (WT) and one transformed with a tpADS+tpFPS gene construct for sesquiterpene content. Similar to FIG. 1, a total ion chromatogram of the transgenic line is compared to that for a control plant. The highest peak corresponds to Amorpha-4,11-diene, while the second highest peak is cubenol. The arrow indicates the presence of $\alpha$-cedrene, which was used as an internal standard.

FIGS. 1 and 2 are the result of a GC-MC analysis and illustrates that plants specifically transformed with plastid targeted genes encoding a specific terpene (patchoulol or amorpha-4,11-diene) synthase of interest and a PRT (farnesyl diphosphate synthase) (A) had an altered terpene content if compared to the wild type (B) and over-accumulated patchoulol and amorpha-4,11-diene, respectively, besides other terpenes synthesised by the same terpene synthase.

Figure 3:
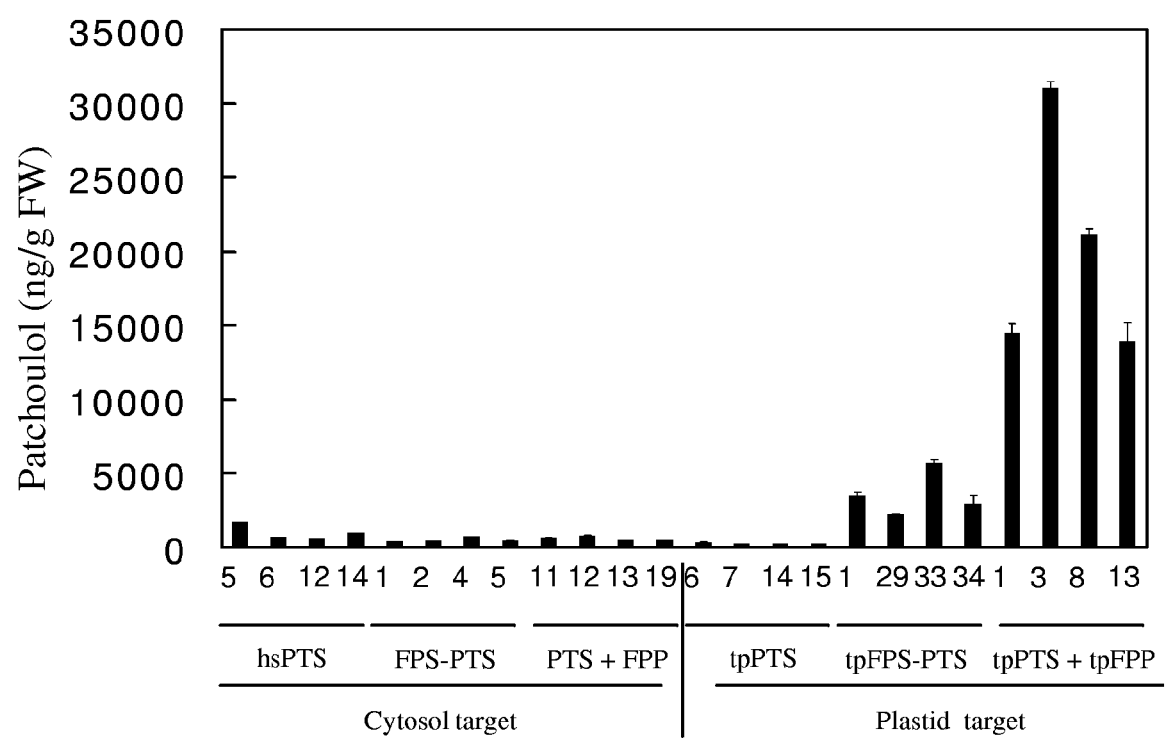
FIG. 3 shows patchoulol content in leaves of plants transformed with different constructs (see detail FIG. 2). The comparison reveals that high yields of patchoulol (>10,000 ng/g of fresh leaf FW) were accumulated in plants transformed with plastid targeted PTS and FPS, be it in the form of distinct gene products or in the form of a fusion protein. Cytosol targeted constructs remained below 2000 ng/g FW.

FIG. 3 is a quantitative analysis of sesquiterpene (patchoulol) content of plants transformed with different constructs. His PTS refers to plants transformed with recombinant genes encoding a patchoulol synthase (PTS) linked to a His-tag. FPSPTS refers to a fusion protein of farnesyl diphosphate sythase (FPS) and PTS, and PTS+FPS refers to plants transformed with individual genes encoding PTS and FPS. On the right hand of the graph, similar constructs further linked to at least one plastid targeting sequence (tp) are shown. Wildtype plants did not accumulate any patchoulol nor any of the other sesquiterpenes associated with the transgenic lines (FIG. 1).

Amorpha-4,11-diene accumulation was also quantified in the plants transformed with tpADS+tpFPS and was found to be approximately 30.mu.g/g FW. More detailed sesquiterpene accumulation of individual transgenic lines are shown in Table 3. Control plants (not shown) did not accumulate any amorpha-4,11-diene.

TABLE 3

Quantiative analysis of amorpha-4,11-diene accumulation in transgenic lines

| Line | Yield ($\mu$g/g) |
|---|---|
| 1a | 11.47 |
| 2 | 11.61 |
| 4a | 25.41 |
| 5 | 27.88 |
| 6m | 6.38 |
| 8 | 6.23 |

Example 8

RNA Extraction and Quantitative RT-PCR Analysis

The total RNA of each line was isolated from 500 mg of young leaves with Trizol reagent according to the manufacturer (Invitrogen Life Technologies, Carlsbad, Calif.). First-strand cDNA was synthesized in 20 $\mu$L reactions with 5 $\mu$g of total RNA, 200 ng of oligodT12-16 primer and Reverse Transcriptase (Superscript II, Invitrogen Life Technologies) in reaction buffer and conditions as recommended by the manufacturer. One $\mu$L of RNase H was subsequently added to the cDNA preparations and incubated at 37° C. for 1 hour to remove complementary RNA.

A quantitative RT-PCR method was used to determine mRNA levels in different transgenic lines. Optimal concentrations for linear PCR amplification were determined by varying the amount of added cDNA template and using number of PCR cycles (10, 15, 20, 25 and 30). The primers PTS-8F and PTS-160R were used to amplify PTS gene, while FPP-1F and FPP-160R) were used for the FPS gene. Another primer pair, RBCS-FW and RBCS-RV, was used to amplify the RUBis CO small subunit gene as an internal standard. Typical PCR conditions consisted of 1× Taq buffer (as supplied by the manufacturer), 1.5 mM $MgCl_2$, 0.2 mM dNTP mixture, 2 $\mu$M of each primers, 1.25 $\mu$L cDNA, and 1 unit Taq DNA polymerase in a total of 25 $\mu$L mixture. PCR amplifications was carried out for 20 temperature cycles, each consisting of denaturation at 94° C. for 30 sec, annealing at 60° C. for 30 sec, and extension at 72° C. for 60 sec. PCR products were separated by agarose gel electrophoresis, stained with ethidium bromide, and photographed.

Figure 4:
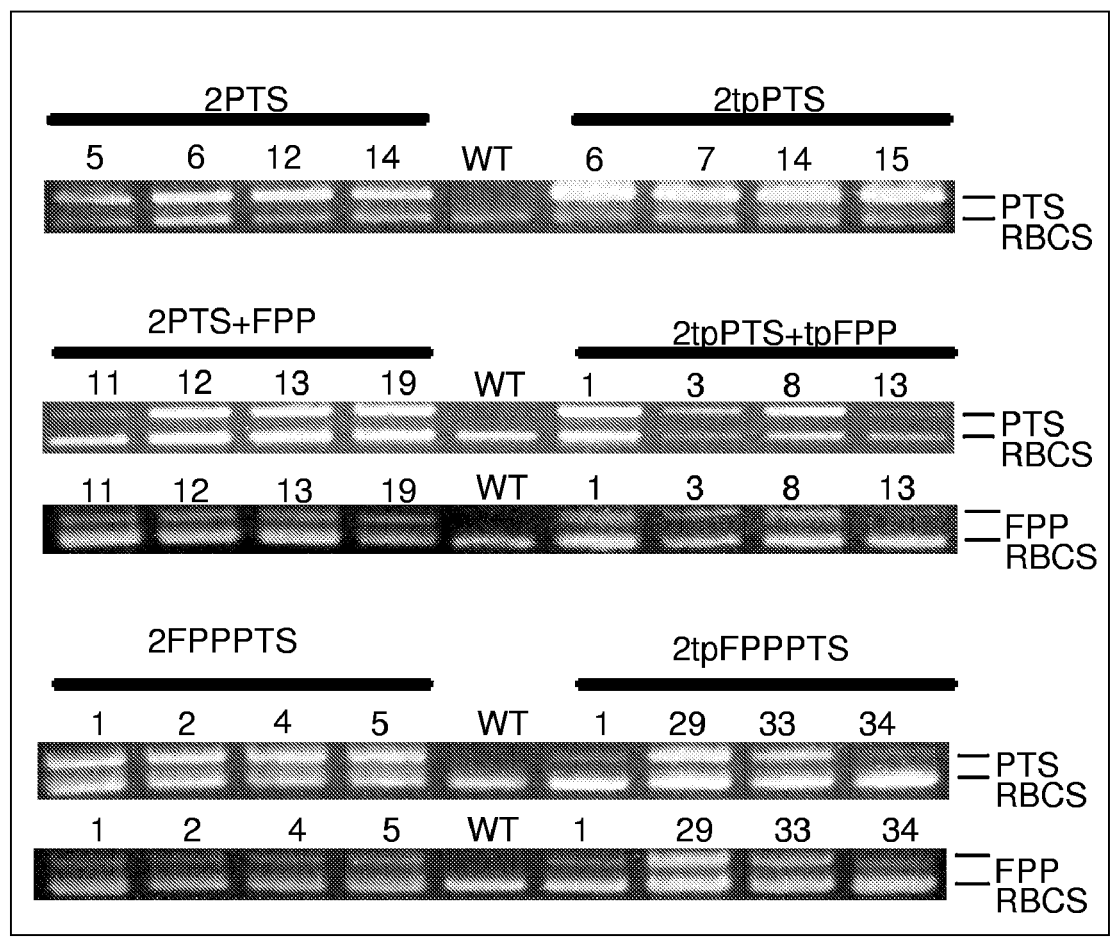
FIG. 4 quantitatively shows the mRNA expression levels in regenerated transgenic plant lines overexpressing a farnesyl diphosphate synthase (FPS), a sesquiterpene (patchoulol) synthase (PTS), or both.

The results of the PTS and FPS mRNA analysis is shown in FIG. 4. The figure shows RT-PCR products derived from mRNA isolated from plants transformed with constructs containing a patchoulol synthase (PTS) gene, or a plastid targeted PTS (tpPTS) gene, or a construct containing a patchoulol synthase and a FPS genes (PTS+FPS), or a construct containing distinct genes for a plastid targeted PTS and FPS (tpPTS+ tpFPS), or a construct encoding for a fusion protein of FPS and PTS (FPS-PTS), or a corresponding, plastid targeted fusion protein (tpFPS-PTS). RBCS is the RT-PCR product derived from the Rubisco small subunit mRNA, present in the wild-type (WT) and transgenic plants, and serves as an internal standard.

It can be seen that wild-type (WT) plants did not express PTS or FPS. Many of the lines harboring the his PTS, PTS+FPS, PTS-FPS and tpPTS constructs expressed readily detectable levels of the PTS mRNA, but patchoulol accumulation was relatively modest and poorly correlated with the PTS mRNA expression levels. In contrast, expression of the plastid targeted tpPTS gene in combination with tpFPS, either as separate genes or as a fusion gene, resulted in similar expression levels of the PTS mRNA and yielded accumulation of significantly higher levels of patchoulol.

Example 9

Protein Expression Analysis

A mixture of 4 to 5 synthesized peptides was used as antigens to prepare antibodies of PTS and FPS. The antigenic peptides were predicted by a free software (http://bio.dfci.harvard.edu/Tools/antigenic.html) and selected by direct 3Dstructural analysis (PDB: 1FPS) for FPS or homology model comparison with an available structure EAS (PDB: 5EAS) for PTS. We designed 5 antigenic peptides (PTS46; PTS108; PTS353; PTS462; PTS475) for PTS, and 4 antigenic peptides (FPP41; FPP59; FPP218; FPP320) for FPS. All the peptides were synthesized in a 10 mg scale at immunological grade by Sigma-Genosys (The Woodland, Tex., US). Each of the peptide mixtures were then conjugated to KLH (Keyhole Limpet Hemocyanin) carrier protein and injected into rabbits by Strategic Biosolutions (Windham, Me.). Polyclonal antibodies for PTS and FPS were further purified by preparative antigenic affinity column prepared with CNBR-activated sepharose 4B resin coupled with purified PTS or FPS protein according to the manufacturer's instruction (Amersham Biosciences, Buckinghamshire, England).

To measure PTS and FPS protein levels in transgenic plant material, 100 mg of young leave material was ground in liquid nitrogen, then extracted with 800 µL of 80 mM potassium phosphate (pH 7.0), 10% glycerol, 10 mM sodium metabisulfide, 15 mM $MgCl_2$, 10 mM sodium ascorbate, 1% polyvinylpyrrolidone, and 14 mM α-mercaptoethanol. The crude protein extracts were centrifuged at 4° C. for 20 min at full speed in a table top microfuge, and the resulting supernatant used as the protein source. Samples containing 40 µg of supernatant protein was electrophoresized in a 15% SDS-PAGE gel and blotted into a nitrocellulose membrane (BIO-RAD, Hercules, Calif.). Membranes were blocked with standard Tween 80/Tris-buffered saline (TTBS) blocking solution containing 5% dried milk before adding the purified PTS or FPS antibody. Membranes were then incubated for 3-7 hrs at room temperature with shaking, washed three times with TTBS, and then incubated with goat peroxidase labeled anti-rabit IgG (Kirkegaard and Perry Laboratories, Gaithersburg, Md.) in TTBS blocking solution for another 3 hours at room temperature. Chemiluminescent detection of the secondary antibody was performed with an ECL reagent kit according to the manufactuer's instructions (Amersham Biosciences, Buckinghamshire, England).

Figure 5:
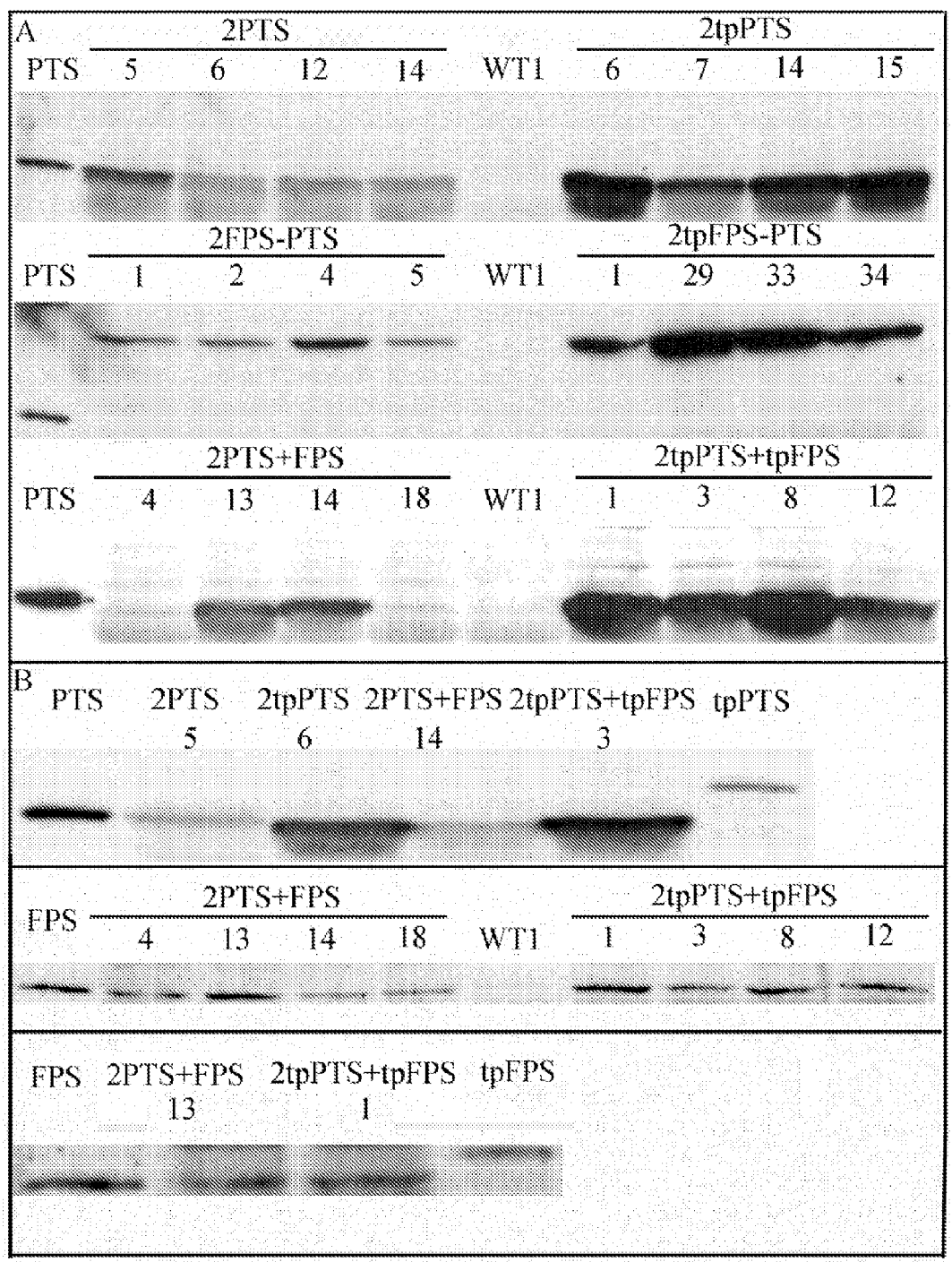
FIG. 5 shows Expression levels and processing of the patchoulol synthase (PTS) and farnesyl diphosphate synthase (FPS) proteins in transgenic plants as measured immunodetection.

Expression levels and processing of the patchoulol synthase (PTS) and farnesyl diphosphate synthase (FPS) proteins in transgenic plants are shown in FIG. 5. The numbers above lanes in FIG. 5 represent independent transgenic plant lines engineered to contain a patchoulol synthase (PTS) gene, or a plastid targeted PTS (tpPTS) gene, or a construct containing a patchoulol synthase and a FPS genes (PTS+FPS), or a construct containing distinct genes for a plastid targeted PTS and FPS (tpPTS+tpFPS), or a construct encoding for a fusion protein of FPS and PTS (FPS-PTS), or a corresponding, plastid targeted fusion protein (tpFPS-PTS). The positive control used are PTS and FPS proteins or the corresponding protein containing an amino-terminal plastid targeting peptide (respectively lanes PTS, FPS, tpPTS, tpFPS) purified from bacteria transformed to over-express these proteins. Lane WT1, extract from the leaves of a wild-type plant. Upper panels show membranes probed with the PTS antibodies and the two membranes in the lower part of the figure show membranes probed with the FPS antibodies. It can be seen in FIG. 5 that no protein was immunologically detected in the wild type plants. For most of the transgenic lines analysed, PTS and/or FPS proteins could be detected in the leaf extracts and the expression pattern was generally consistent with the patchoulol accumulation. Interestingly, the apparent molecular weight of the PTS and FPS proteins detected in plants transformed with constructs containing the corresponding genes linked to a plastid targeted sequence (for example the lines 2tpPTS and 2tpPTS+tpFPS), are identical to the molecular weight of the same protein expressed in plants or bacteria without plastid targeting signal (for example PTS, 2PTS or 2PTS+FPS). In addition, expression of the PTS or FPS with plastid targeting peptide in bacteria (which can not cleave the targeting peptide) leads to proteins having clearly a higher molecular weight. These observations show that the chloroplast targeted proteins were effectively processed and thus, that these proteins are actually transported to the plastids.

Example 10

[1-$^{13}$C]-Glucose Labelling for Showing Pathway Used for Terpene Synthesis in Plants of the Present Invention Seeds of 8PTS10 (transgenic plant lines expressing PTS in the cytosol) and 2tpPTS+tpFPS12 (plastidic) were germinated on solid MS medium with the addition of hygromycin (15 mg/l).

For GC-MS analysis, thirty 4-week-old seedlings were subsequently transferred to 25 ml flasks containing 5 ml of liquid MS medium without sucrose and incubated with gentle shaking (125 rpm) in the dark. One day later, 100 mg of [1-$^{13}$C]-glucose (Sigma) was added into media and plant material collected at daily intervals. For GC analysis, 100 mg samples were extracted as described in Example 7.

For NMR analysis, 1000 seedlings of above two transgenic lines were used, with 100 seedling grown in a 250 ml flask containing 50 ml of liquid MS medium with the addition of 1 g [1-$^{13}$C]-glucose. All labeled seedlings were collected after one week and extracted as above. Concentrated extracts (3 ml) were then purified by preparative TLC separations using silica TLC plates and hexane:ethylacetate (9:1) as the developing solvent.

250 µg of purified $^{13}$C-labeled patchoulol from line 2tpPTS+tpFPS12 and 500 µg from 8PTS10 were subsequently analyzed by $^{13}$C-NMR (750 mHz, $CDCl_3$ by Bob Coates in the Chemistry Department, University of Illinois, Champaign, Ill.). Carbon positions and enrichments were assigned relative to un-labeled patchoulol purified from control plants.

Figure 6:
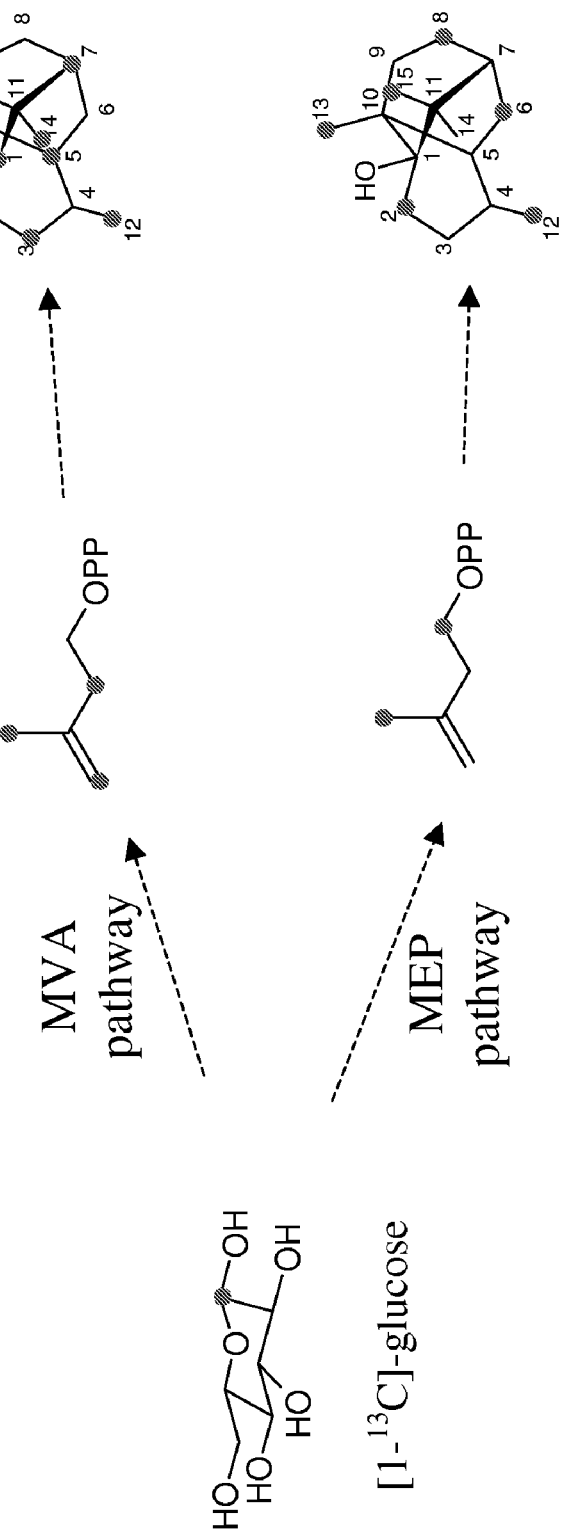
FIG. 6 shows predicted $^{13}$C-labeling patterns in patchoulol bio-synthesised through the MEP or MVA pathway in seedlings grown on [1-$^{13}$C]-glucose.

FIG. 6 shows the predicted $^{13}$C labelling patterns in patchoulol synthesised from IPP emerging from the MVA and the MEP pathway, respectively, in transgenic seedlings fed on [1-$^{13}$C]-glucose. Patchoulol synthesised from IPP of the MVA pathway is predicted to have 9 $^{13}$C-carbons at positions 1, 3, 5, 7, 9, 12, 13 14 and 15, whereas its counterpart from the MEP pathway is expected to have only 6 $^{13}$C-carbons, namely art positions 2, 6, 8, 12, 13 and 15.

Figure 7:
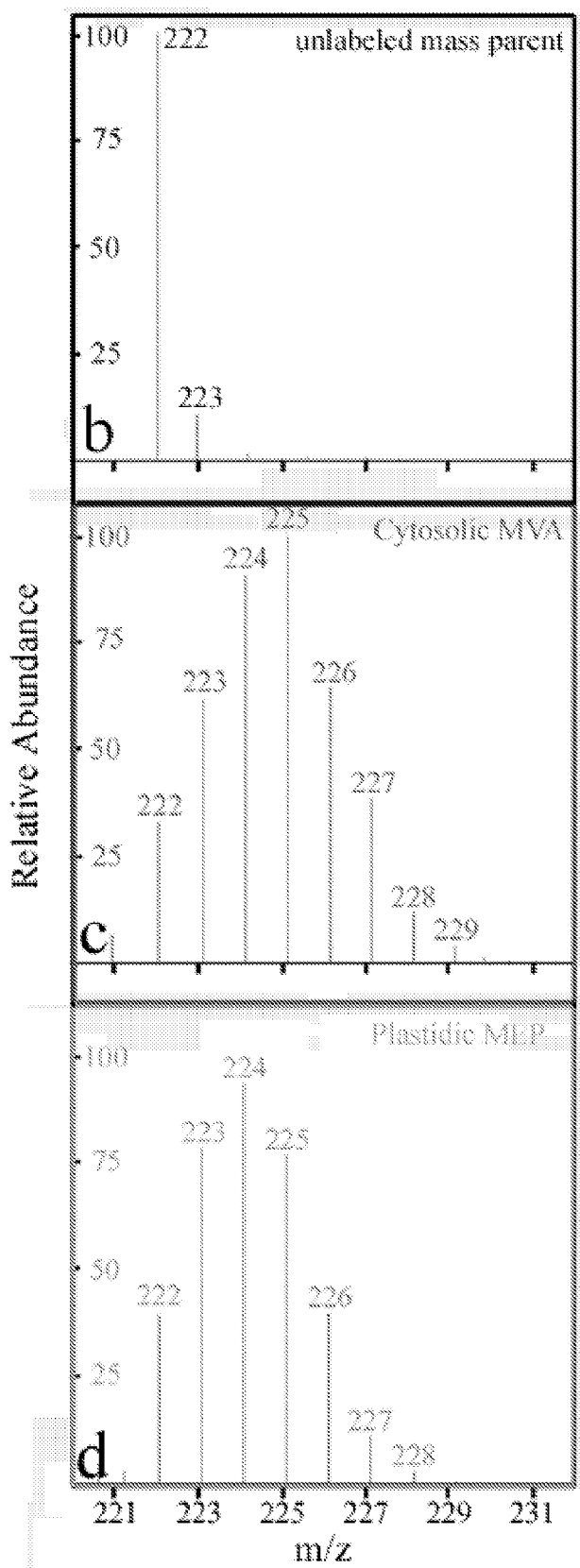
FIG. 7 compares MS parent ions for patchoulol synthesized by plants fed $^{12}$C-glucose (upper panel), versus synthesis from [1-$^{13}$C]-glucose by plants engineered for cytosolic (middle) or plastidic (bottom) biosynthesis.

Results of GC-MS analysis are shown in FIG. 7, in which FIG. 7b shows MS parent ions for patchoulol synthesised by plants fed $^{12}$C-glucose (control) and FIGS. 7 c and d plants fed on $^{13}$C-glucose producing patchoulol by the (cytosolic) MVA and (plastidic) MEP pathway, respectively. It can be seen that patcholoul emerging from plants fed on $^{13}$C have heavier ions, with the effect being less pronounced with the plastidic patchoulol: the mass of the major parent ion is shift from 222 to 225, and an M+8 mass parent ion can be observed when the cytosolic pathway is engineered; and the mass of the major parent ion is shifted to 224 and an M+6 mass parent ion can be observed when the chloroplast pathway is engineered. These observation are consistent with the labelling prediction. Results of NRM-analysis are shown in Table 2 below.

TABLE 2

$^{13}$C enrichment into pachoulol synthesized by the cytosoloic MVA and plastidic MEP pathways from 1-C$^{13}$-glucose

| | | % $^{13}$C | |
|---|---|---|---|
| Carbon atom | Dc (ppm) | 8PTS-10 | 2tpPTS + tpFPS-12 |
| 1 | 74.9 | 13.0 | 0.0 |
| 2 | 33.1 | 3.0 | 13.8 |
| 3 | 28.9 | 21.8 | 4.2 |
| 4 | 28.1 | 2.9 | 2.7 |
| 5 | 43.8 | 19.1 | 2.4 |
| 6 | 24.5 | 22.2* | 18.4 |
| 7 | 39.4 | 19.3 | 2.7 |
| 8 | 24.9 | 2.9 | 17.3 |
| 9 | 29.1 | 17.1 | 3.6 |
| 10 | 37.8 | 1.6 | 2.0 |
| 11 | 40.3 | 1.4 | 4.0 |
| 12 | 18.8 | 22.9 | 19.1 |
| 13 | 20.9 | 20.2 | 17.9 |
| 14 | 27.3 | 22.0 | 6.1 |
| 15 | 24.7 | 15.8 | 13.8 |

*signal due to contaminate

In accordance with predicted labelling patterns shown in FIG. 6, Table 2 shows that in patchoulol from plants having PTS and FPS targeted to the plastids, carbon atoms 2, 6, 8, 12, 13 and 15 are enriched with 13C. The labelling thus shows that the sesquiterpene is actually synthesised from IPP resulting from the MEP-pathway and hence, in the plastids.

Example 11

Plant Plastidic Genomes Transformed with PTS and FPS Genes

The system of recombination cloning into the plastid genome developed by the Maliga laboratory (Lutz et al 2004) has been used and modified. We used *Nicotiana tobacco* LA63 as the recipient tobacco host material. LA63 has one attB site integrated in chloroplast genome DNA allowing for foreign DNA insertion into this site. A suitable transformation vector was re-constructed as shown in (FIG. 15 I-III). We included an IPTG inducible Prrn promoter based on previously published work (Muhlbauer and Koop 2005) for providing for regulated gene expression.
11.1 Construction of the Plastid Transformation Vectors A universal plastid transformation vector pLvec (FIG. 15 I-III) was constructed, using the pT7Blue (Novagen, Madison, Wis.) vector as the backbone.

FIG. 15 Part I:

The pT7Blue vector DNA was digested with the HindIII restriction enzyme. Following treatment with T4 polymerase and self-ligation, the HindIII restrict enzyme site was knocked out and the resulting plasmid designated as ΔHindIII pT7Blue.

A linker consisting of two primers (pLlinkF and pLlinkR) were introduced into the EcoRI/KpnI sites of pT7blue to create new multiple cloning sites SgfI-BamHI-SpeI-NotI-SmaI. The previous EcoRI site was simultaneously removed by linker designing (the last C for the EcoRI recognition sequence was removed). The generated vector was designated as pLlink.

The attP recombination site was amplified by primer attP-XbaF and Attp-SphR and ligated into the XbaI-SphI sites of pLlink vector and designated as pLattP An aada cassette (including Prm promoter and Trbc1 terminator) was amplified using Primer Prrn-XbaF and TrbcL-KpnR and ligated into the pLattP XbaI-KpnI site to make vector pLattP+aadA.

The Prm promoter was amplified a second time with primer Prrn-KpnF and Prrn-SmaR. After digestion with the corresponding restriction enzymes, this fragment was ligated into the Kpn-SmaI sites of pLattP+aadA to make pLattP+aadA+prrn.

FIG. 15 Part II:

The *Nicotiana tabacum* ATP synthase alpha subunit operon terminator (Tatp) was amplified from tobacco with primers Tatp-SmaF and Tatp-NotR. This fragment was ligated into SmaI-NotI site of vector pLattp+aadA+prrn+Tatp.

Lac repressor gene (LacI) gene was amplified from *E. coli* with primers Lacd-SmaF and LacI-SmaR. After digestion with SmaI, this fragment was ligated into the SmaI site of pLattp+aada+prrn+Tatp to make vector pLattp+aadA+LacI.

A new terminator Trbc1 was amplified from tobacco with primer Trbc1-SpeF and Trbc1-NotR. The amplified fragment was digested with SpecI and NotI, and ligated into the vector pLattp+aadA+LacI to make pLattP+aadA+lacI+Trbcl.

Based on the publication of Muhlbauer and Koop (2005), an IPTG inducible primer PrmlacI was generated by two-successive PCR amplification with PrrnlacI-SgfF as forward primer and PrrnlacI-R1nest following PrmlacI-BamHR as reverse primer. After digestion, PrmlacI was ligated into the SgfI-BamHI sites of pLattp+aadA+LacI+Trbcl to make the universal vector pLvec (FIG. 15 parts II and III).

FIG. 15 Part III:

GUS gene was amplified from Ti vector of pB121 with primer GUS-BamF and GUS-SpeR. After digestion with corresponding strict enzymes, the GUS gene was ligated into the pLvec vector to make construct pLGUS.

A FPS-(AscI)-PTS fragment was amplified from ptpFPS+tpPTS construct for nuclear transformation with primers FPS-BamF and PTS-SpeR. After digestion with corresponding strict enzymes, FPS-(AscI)-PTS was ligated into pLvec to make construct pLFPS-PTS.

A Trbc1-(SpeI)-PrrnlacI construct was constructed in a T/A helper vector. Trbc1 was first PCR amplified using Trbc1-AscF and Trbc1-SpeR and T/A cloned into the pGEM-T Easy vector (Promega). To obtain sequence orientation, a clone harboring the Trbc1 gene 5' to 3' from the T7 promoter to the SP6 promoter was identified and used for the next ligation. This intermediate vector was designated as pTTrbcl. Another gene PrrnlacI was amplified in a same way as described above by using primers PrrnlacI-SpeF and Prrn-lac-AscI-SpeR. After digestion with SpecI, PrrnLacI was ligated into the SpecI site of pTTrbcl. A clone having the correct orientation was identified by strategic restriction enzyme digestion and designated as pTTrbcl-(SpeI)-PrrnlacI.

After digestion of pTTrbcl-(SpeI)-PrrnlacI with AscI, the Trbc1-(SpeI)-PrrnlacI fragment was ligated into the pLFPS-PTS AscI site to make the final construct LFPS+PTS.
11.2 Methods for Plastid Transformation
DNA Preparation and Gold Treatment 7.5 mg (sufficient for 9 shots) of 1.0 micron gold particles (Bio-rad, Hercules, Calif.) were first sterilized with 1 ml ethanol. After centrifuging, the ethanol was removed and 111 μl fresh ethanol was added. The gold particles were separated into three equal sized aliquots, each with 35 μl ethanol/gold mixture. 1.0 ml of sterilize water was added to each of the ethanol/gold aliquots. After centrifuge 5 min at 200 rpm, the water/ethanol supernatant was removed and gold particles were ready for DNA coating. Five μls of plasmid DNA (pL-GUS or pLFPS+PTS, ca. 1 μg/μl), 220 μl sterilized water, 250 μl CaCl$_2$ (2.5M), 100 μl Spermidine (IM) were added in order and mixed thoroughly. The DNA/gold mixture was then incubated on ice for 2 min, followed by centrifugation (5 min, 1000 rpm) and removal of the supernatant. The DNA/gold pellet was then rinsed with 600 μl ethanol and resuspended in 36 μl of ethanol and placed on ice for 1 hour before using for shooting (bioballistic treatment).

During DNA/gold precipitation on ice, plant materials were prepared. One-month old sterile tobacco leaves of line LA63 were cut and placed on water-wetted filter paper (5 cm I.D.) in a petri dish.

10 μl of ice-treated DNA/gold pellet in ethanol was transferred into micro carries and shot into the leaf material using a particle delivery system (Gene Gun) (model PDS-1000, Dupont) following manufacturer's instructions.

"Shot" leaf segments were transferred onto TOM medium and incubated in the dark for 24 hrs.

Leaf segments were then cut into small pieces and transferred into TOM media containing spectinomycin (500 ng/l) for callus generation.

Leaf segments were transferred to fresh selection plates every 15 days until plant shoots were visible.

Regenerated shoots were transferred into rooting medium with same spectinomycin selection.

Regenerated plantlets were assessed for GUS expression or terpene accumulation as described above. For GUS expression test, GUS staining methods was used. First, the regenerated leaves or shoots (only for GUS construction) were incubated with liquid TOM media with spectinomycin (500 ng/l) and also with 1 mM IPTG for induction for 3 days. The induced shoots/leaves were moved into GUS staining solution (50 mM potassium phosphate buffer, 12 mM 2-mecarptoethanol, 0.1% Triton X-100, 500 μg/ml 5-bromo-4-chloro-3-indolyl-b-D-glucuronide (Research Products International Corp., Mt. Prospect, Ill.), 2.5 μM potassium ferricyanide, 2.5 μM potassium ferrocyanide) for another day of incubation, then destained in 70% ethanol.

Positive transformants of the plastidic genome showed blue staining. It was thus shown that plastidic genomic DNA of plants were transformed to harbour heterologous genes encoding a sesquiterpene synthase and a farnesyl diphosphate synthase.

Example 12

Insect Repellent Test

Three healthy leaves of the approximate same developmental age (W 5 cm×L 8 cm) were collected for line 2tpPTS+tpFPS-12 and wild type 14-2, then placed within an equal distance of one another (ca. 1 cm) within an enclosed box. Six commercially available hornworms (*Manduca sexta*) (Carolina Bilogical Supply Company, Burlington, N.C.), at the second instar stage of development were placed onto each leaf evenly so that each hornworms had an equal opportunity to eat the leaf or move to another. The experiment was run for 6 hr before counting the digested leaf areas and recording hornworm numbers on each leaf after migration.

REFERENCES

Ausubel F M, Brent R, Kingston R E, Moore D D, Seidman J G, Smith J A, Struhl K (1987) Current Protocols in Molecular Biology.

Benfey P N, Chua N H (1990) The Cauliflower Mosaic Virus-35s Promoter—Combinatorial Regulation Of Transcription In Plants. Science 250: 959-966

Chappell J, Wolf F, Proulx J, Cuellar R, Saunders C (1995) Is The Reaction Catalyzed By 3-Hydroxy-3-Methylglutaryl Coenzyme-A Reductase A Rate-Limiting Step For Isoprenoid Biosynthesis In Plants. Plant Physiology 109: 1337-1343

Chin D J, Gil G, Russell D W, Liscum L, Luskey K L, Basu S K, Okayama H, Berg P, Goldstein J L, Brown M S (1984) Nucleotide-Sequence Of 3-Hydroxy-3-Methyl-Glutaryl Coenzyme-A Reductase, A Glycoprotein Of Endoplasmic-Reticulum. Nature 308: 613-617

Frey P M, Scharer-Hernandez N G, Futterer J, Potrykus I, Puonti-Kaerlas J (2001) Simultaneous analysis of the bidirectional African cassaya mosaic virus promoter activity using two different luciferase genes. Virus Genes 22: 231-242

Hajdukiewicz P, Svab Z, Maliga P (1994) The Small, Versatile Ppzp Family Of *Agrobacterium* Binary Vectors For Plant Transformation. Plant Molecular Biology 25:

Hartley J L, Temple G F, Brasch M A (2000) DNA cloning using in vitro site-specific recombination. Genome Research 10: 1788-1795

Horsch R B, Fry J E, Hoffmann N L, Eichholtz D, Rogers S G, Fraley R T (1985) A Simple And General-Method For Transferring Genes Into Plants. Science 227: 1229-1231

Lucker et al (2001) Expression of Clarkia S-linalool synthase in transgenic petunia plants results in the accumulation of S-linalyl-beta-D-glucopyranoside; Plant J. 4: 315-24

Lutz et al (2004) Plant J. 37: 906-913

Mau C J, West C A (1994) Cloning of casbene synthase cDNA: evidence for conserved structural features among terpenoid cyclases in plants Proc Natl Acad Sci USA; 91(18):8497-501.

Mersereau M, Pazour G J, Das A (1990) Efficient Transformation Of *Agrobacterium*-Tumefaciens By Electroporation. Gene 90: 149-151

Muhlbauer and Koop (2005) Plant J. 43: 941-946

Murashige T, Skoog F (1962) A Revised Medium For Rapid Growth And Bio Assays With Tobacco Tissue Cultures. Physiologia Plantarum 15: 473-&

Ohara et al (2003) Limonene production in tobacco with *Perilla* limonene synthase cDNA. J. Exp. Bot.

Peters et al (2000) Biochemistry; 39(50): 15592-602

Sambrook J, Fritsch E F, Maniatis T (1989) Molecular Cloning—a laboratory manual (2nd Edition). Cold Spring Harbor Press, Cold Spring Harbor, N.Y.

Schardl C L, Byrd A D, Benzion G, Altschuler M A, Hildebrand D F, Hunt A G (1987) Design And Construction Of A Versatile System For The Expression Of Foreign Genes In Plants. Gene 61: 1-11

Shirai, K., Masuda, K. and Oosawa, K. 2002. Cloning and Sequencing of Ent-kKaurene Synthase cDNA from Cucumber. Acta Hort. (ISHS) 588: 317-320

Takahashi S, Zhao Y, O'Maille P E, Greenhagen B T, Noel J P, Coates R M, Chappell J (2005) Kinetic and molecular analysis of 5-epiaristolochene-1,3-dihydroxylase, a cytochrome P450 enzyme catalyzing successive hydroxylations of sesquiterpenes. Journal of Biological Chemistry 280: 3686-3696

Tarshis L C, Yan M J, Poulter C D, Sacchettini J C (1994) Crystal-Structure Of Recombinant Farnesyl Diphosphate Synthase At 2.6-Angstrom Resolution. Biochemistry 33: 10871-10877

The invention claimed is:

1. A transformed plant accumulating patchoulol, which is transformed to comprise at least one nucleotide sequence encoding a farnesyl diphosphate synthase (FPS) and a patchoulol synthase, both targeted to plant plastids, wherein said nucleotide sequence comprises SEQ ID NO:1 and wherein said transformed plant accumulates at least 10,000 ng/g of fresh leaf of patchoulol.

2. The transformed plant according to claim 1, in which patchoulol is, at least in part, bio-synthesised via the MEP pathway.

3. The transformed plant according to claim 1, in which the FPS is a non-plant prenyl transferase.

4. The transformed plant according to claim 1, in which the at least one nucleotide sequence is integrated into plant plastidic DNA.

5. A vector comprising at least one nucleotide sequence comprising SEQ ID NO:1 and encoding a farnesyl diphosphate synthase (FPS) and a patchoulol synthase, or a fusion protein of a FPS and a patchoulol synthase, with the nucleotide sequence further comprising a plastid targeting sequence linked in frame to the nucleotide sequence encoding the FPS, the patchoulol synthase, or the fusion protein.

6. A method for altering the content of patchoulol in a plant so that said plant accumulates at least 10,000 ng/g of fresh leaf of patchoulol, which comprises:

transforming plant material with at least one DNA construct comprising at least one nucleotide sequences encoding a FPS and a patchoulol synthase, targeted to plant plastids, said DNA construct comprising SEQ ID NO:1 and regenerating a transformed plant from the transformed plant material.

7. A method of producing patchoulol which comprises providing a transformed plant according to the method of claim 6 and isolating patchoulol from the transformed plant.

8. A method for producing a plant having an altered patchoulol content and accumulating at least 10,000 ng/g of fresh leaf, which comprises:

transforming plant material with at least one DNA construct comprising at least one nucleotide sequences encoding a FPS and a patchoulol synthase, targeted to plant plastids, said DNA construct comprising SEQ ID NO:1 and regenerating a transformed plant from the transformed plant material.

9. A method of producing patchoulol which comprises providing a transformed plant according to the method of claim 8 and isolating patchoulol from the transformed plant.

10. A method of producing patchoulol, which comprises isolating patchoulol from the plant of claim 1.

* * * * *

UNITED STATES PATENT AND TRADEMARK OFFICE
CERTIFICATE OF CORRECTION

| | | |
|---|---|---|
| PATENT NO. | : 8,017,835 B2 | Page 1 of 1 |
| APPLICATION NO. | : 11/911660 | |
| DATED | : September 13, 2011 | |
| INVENTOR(S) | : Chappell et al. | |

It is certified that error appears in the above-identified patent and that said Letters Patent is hereby corrected as shown below:

Title Page:
Item (75) Inventors: correct the spelling of the first name of inventor Clark from "Athony" to -- Anthony --. The inventor's name will then correctly appear as "Anthony Clark".

Add the following item before Item (30):
    -- Related U.S. Application Data
(60)   Provisional application no. 60/673,019, filed Apr. 19, 2005 --.

Signed and Sealed this
Twenty-ninth Day of May, 2012

David J. Kappos
*Director of the United States Patent and Trademark Office*

SEQUENCE LISTING

<160> NUMBER OF SEQ ID NOS: 79

<210> SEQ ID NO 1
<211> LENGTH: 1845
<212> TYPE: DNA
<213> ORGANISM: Artificial
<220> FEATURE:
<223> OTHER INFORMATION: Patchoulol synthase cDNA of Pogostemon cablin
      linked to a plastid transit peptide sequence

<400> SEQUENCE: 1

| | | | | | |
|---|---|---|---|---|---|
| atggcttcct | ctatgctctc | ctccgccgct | gtggttacat | ccccggctca | ggccaccatg | 60 |
| gtcgctccat | tcaccggctt | gaagtcatcc | gctgcattcc | cggtcacccg | caagaccaac | 120 |
| aaggacatca | cttccatcgc | aagcaacggg | gaagatcta | gctgcatgaa | ggagctcggc | 180 |
| gcgcctatgg | agttgtatgc | ccaaagtgtt | ggagtgggtg | ctgcttctcg | tcctcttgcg | 240 |
| aattttcatc | catgtgtgtg | gggagacaaa | ttcattgtct | acaacccaca | atcatgccag | 300 |
| gctggagaga | gaagaggc | tgaggagctg | aaagtggagc | tgaaaagaga | gctgaaggaa | 360 |
| gcatcagaca | actacatgcg | gcaactgaaa | atggtggatg | caatacaacg | attaggcatt | 420 |
| gactatcttt | tgtggaaga | tgttgatgaa | gctttgaaga | atctgtttga | aatgtttgat | 480 |
| gctttctgca | agaataatca | tgacatgcac | gccactgctc | tcagctttcg | ccttctcaga | 540 |
| caacatggat | acagagtttc | atgtgaagtt | tttgaaaagt | ttaaggatgg | caaagatgga | 600 |
| tttaaggttc | caaatgagga | tggagcggtt | gcagtccttg | aattcttcga | agccacgcat | 660 |
| ctcagagtcc | atggagaaga | cgtccttgat | aatgcttttg | acttcactag | gaactacttg | 720 |
| gaatcagtct | atgcaacttt | gaacgatcca | accgcgaaac | aagtccacaa | cgcattgaat | 780 |
| gagttctctt | ttcgaagagg | attgccacgc | gtggaagcaa | ggaagtacat | atcaatctac | 840 |
| gagcaatacg | catctcatca | caaaggcttg | ctcaaacttg | ctaagctgga | tttcaacttg | 900 |
| gtacaagctt | tgcacagaag | ggagctgagt | gaagattcta | ggtggtggaa | gactttacaa | 960 |
| gtgcccacaa | agctatcatt | cgttagagat | cgattggtgg | agtcctactt | ctgggcttcg | 1020 |
| ggatcttatt | tcgaaccgaa | ttattcggta | gctaggatga | ttttagcaaa | agggctggct | 1080 |
| gtattatctc | ttatggatga | tgtgtatgat | gcatatggta | cttttgagga | attacaaatg | 1140 |
| ttcacagatg | caatcgaaag | gtgggatgct | tcatgtttag | ataaacttcc | agattacatg | 1200 |
| aaaatagtat | acaaggccct | tttggatgtg | tttgaggaag | ttgacgagga | gttgatcaag | 1260 |
| ctaggcgcac | catatcgagc | ctactatgga | aaagaagcca | tgaaatacgc | cgcgagagct | 1320 |
| tacatggaag | aggcccaatg | gagggagcaa | aagcacaaac | ccacaaccaa | ggagtatatg | 1380 |
| aagctggcaa | ccaagacatg | tggctacata | actctaataa | tattatcatg | tcttggagtg | 1440 |
| gaagagggca | ttgtgaccaa | agaagccttc | gattgggtgt | tctcccgacc | tcctttcatc | 1500 |
| gaggctacat | taatcattgc | caggctcgtc | aatgatatta | caggacacga | gtttgagaaa | 1560 |
| aaacgagagc | acgttcgcac | tgcagtagaa | tgctacatgg | aagagcacaa | agtggggaag | 1620 |
| caagaggtgg | tgtctgaatt | ctacaaccaa | atggagtcag | catggaagga | cattaatgag | 1680 |
| gggttcctca | gaccagttga | atttccaatc | cctctacttt | atcttattct | caattcagtc | 1740 |
| cgaacacttg | aggttattta | caagagggc | gattcgtata | cacacgtggg | tcctgcaatg | 1800 |
| caaaacatca | tcaagcagtt | gtaccttcac | cctgttccat | attaa | | 1845 |

<210> SEQ ID NO 2
<211> LENGTH: 1314

```
<212> TYPE: DNA
<213> ORGANISM: Artificial
<220> FEATURE:
<223> OTHER INFORMATION: Farnesyl diphosphate cDNA of Gallus gallus
      linked to a plastid transit peptide sequence

<400> SEQUENCE: 2
atggcttcct ctatgctctc ctccgccgct gtggttacat ccccggctca ggccaccatg      60
gtcgctccat tcaccggctt gaagtcatcc gctgcattcc cggtcacccg caagaccaac     120
aaggacatca cttccatcgc aagcaacggg ggaagatcta gctgcatgaa gactagtatg     180
cagccccatc atcatcataa agaggggcgt atgcataaat ttactggtgt caatgccaag     240
tttcagcaac ccgcgttgag gaacctcagc cccgtggtgg ttgagaggga gagggaggag     300
ttcgtggggt tcttcccgca gatcgtccgc gatctgaccg aggacggcat cggacacccg     360
gaggtgggcg acgctgtggc gcggctgaag gaggtgctgc aatacaacgc tcccggtggg     420
aaatgcaacc gtgggctgac ggtggtggct gcgtaccggg agctgtcggg gccggggcag     480
aaggatgctg agagcctgcg gtgcgcgctg gccgtgggtt ggtgcatcga gttgttccag     540
gccttcttcc tggtggctga tgatatcatg gatcagtccc tcacgcgccg ggggcagctg     600
tgttggtata agaaggaggg ggtcggtttg gatgccatca cgactccttc ctcctcgag     660 tcctctgtgt acagagtgct gaagaagtac tgcaggcagc ggccgtatta cgtgcatctg     720
ttggagctct tcctgcagac cgcctaccag actgagctcg gcagatgctg ggacctcatc     780
acagctcccg tctccaaagt ggatttgagt cacttcagcg aggagaggta caaagccatc     840
gttaagtaca agactgcctt ctactccttc tacctacccg tggctgctgc catgtatatg     900
gttgggatcg acagtaagga agaacacgag aatgccaaag ccatcctgct ggagatgggg     960
gaatacttcc agatccagga tgattacctg gactgctttg ggaccccggc gctcacgggg    1020
aaggtgggca ccgacatcca ggacaataaa tgcagctggc tcgtggtgca gtgcctgcag    1080
cgcgtcacgc cggagcagcg gcagctcctg gaggacaact acggccgtaa ggagcccgag    1140
aaggtggcga aggtgaagga gctgtatgag gccgtgggga tgagggctgc gttccagcag    1200
tacgaggaga gcagctaccg gcgcctgcag gaactgatag agaagcactc gaaccgcctc    1260
ccgaaggaga tcttcctcgg cctggcacag aagatctaca aacgccagaa atga          1314

<210> SEQ ID NO 3
<211> LENGTH: 2979
<212> TYPE: DNA
<213> ORGANISM: Artificial
<220> FEATURE:
<223> OTHER INFORMATION: Fused patchoulol synthase (Progostemon cablin)
      and farnesyl disphophate synthase (Gallus gallus) cDNA including
      a plastid transit peptide sequence

<400> SEQUENCE: 3
atggcttcct ctatgctctc ctccgccgct gtggttacat ccccggctca ggccaccatg      60
gtcgctccat tcaccggctt gaagtcatcc gctgcattcc cggtcacccg caagaccaac     120
aaggacatca cttccatcgc aagcaacggg ggaagatcta gctgcatgaa gactagtatg     180
cagccccatc atcatcataa agaggggcgt atgcataaat ttactggtgt caatgccaag     240
tttcagcaac ccgcgttgag gaacctcagc cccgtggtgg ttgagaggga gagggaggag     300
ttcgtggggt tcttcccgca gatcgtccgc gatctgaccg aggacggcat cggacacccg     360
gaggtgggcg acgctgtggc gcggctgaag gaggtgctgc aatacaacgc tcccggtggg     420
aaatgcaacc gtgggctgac ggtggtggct gcgtaccggg agctgtcggg gccggggcag     480
```

```
aaggatgctg agagcctgcg gtgcgcgctg gccgtgggtt ggtgcatcga gttgttccag    540
gccttcttcc tggtggctga tgatatcatg gatcagtccc tcacgcgccg ggggcagctg    600
tgttggtata agaaggaggg ggtcggtttg gatgccatca acgactcctt cctcctcgag    660
tcctctgtgt acagagtgct gaagaagtac tgcaggcagc ggccgtatta cgtgcatctg    720
ttggagctct tcctgcagac cgcctaccag actgagctcg gcagatgctg gacctcatc    780 acagctcccg tctccaaagt ggatttgagt cacttcagcg aggagaggta caaagccatc    840
gttaagtaca agactgcctt ctactccttc tacctacccg tggctgctgc catgtatatg    900
gttgggatcg acagtaagga agaacacgag aatgccaaag ccatcctgct ggagatgggg    960
gaatacttcc agatccagga tgattacctg gactgctttg gggacccggc gctcacgggg   1020
aaggtgggca ccgacatcca ggacaataaa tgcagctggc tcgtggtgca gtgcctgcag   1080
cgcgtcacgc cggagcagcg gcagctcctg gaggacaact acggccgtaa ggagcccgag   1140
aaggtggcga aggtgaagga gctgtatgag gccgtgggga tgagggctgc gttccagcag   1200
tacgaggaga gcagctaccg gcgcctgcag gaactgatag agaagcactc gaaccgcctc   1260
ccgaaggaga tcttcctcgg cctggcacag aagatctaca aacgccagaa aggcgcgccg   1320
atggagttgt atgcccaaag tgttggagtg ggtgctgctt ctcgtcctct tgcgaatttt   1380
catccatgtg tgtggggaga caaattcatt gtctacaacc cacaatcatg ccaggctgga   1440
gagagagaag aggctgagga gctgaaagtg gagctgaaaa gagagctgaa ggaagcatca   1500
gacaactaca tgcggcaact gaaaatggtg gatgcaatac aacgattagg cattgactat   1560 cttttttgtgg aagatgttga tgaagctttg aagaatctgt ttgaaatgtt tgatgctttc   1620
tgcaagaata tcatgacat gcacgccact gctctcagct ttcgccttct cagacaacat   1680
ggatacagag tttcatgtga agttttttgaa aagtttaagg atggcaaaga tggatttaag   1740
gttccaaatg aggatggagc ggttgcagtc cttgaattct tcgaagccac gcatctcaga   1800
gtccatggag aagacgtcct tgataatgct tttgacttca ctaggaacta cttggaatca   1860
gtctatgcaa cttttgaacga tccaaccgcg aaacaagtcc acaacgcatt gaatgagttc   1920
tcttttcgaa gaggattgcc acgcgtgaa gcaaggaagt acatatcaat ctacgagcaa   1980
tacgcatctc atcacaaagg cttgctcaaa cttgctaagc tggatttcaa cttggtacaa   2040
gctttgcaca aaggggagct gagtgaagat tctaggtggt ggaagacttt acaagtgccc   2100
acaaagctat cattcgttag agatcgattg gtggagtcct acttctgggc ttcgggatct   2160
tatttcgaac cgaattattc ggtagctagg atgattttag caaaagggct ggctgtatta   2220
tctcttatgg atgatgtgta tgatgcatat ggtacttttg aggaattaca aatgttcaca   2280
gatgcaatcg aaaggtggga tgcttcatgt ttagataaac ttccagatta catgaaaata   2340
gtatacaagg ccctttttgga tgtgtttgag gaagttgacg aggagttgat caagctaggc   2400
gcaccatatc gagcctacta tggaaaagaa gccatgaaat acgccgcgag agcttacatg   2460
gaagaggccc aatggaggga gcaaaagcac aaacccacaa ccaaggagta tatgaagctg   2520
gcaaccaaga catgtggcta cataactcta ataatattat catgtcttgg agtggaagag   2580
ggcattgtga ccaaagaagc cttcgattgg gtgttctccc gacctccttt catcgaggct   2640
acattaatca ttgccaggct cgtcaatgat attacaggac acgagtttga gaaaaaacga   2700
gagcacgttc gcactgcagt agaatgctac atggaagagc acaaagtggg gaagcaagag   2760
gtggtgtctg aattctacaa ccaaatggag tcagcatgga aggacattaa tgaggggttc   2820
ctcagaccag ttgaatttcc aatccctcta ctttatctta ttctcaattc agtccgaaca   2880
```

```
cttgaggtta tttacaaaga gggcgattcg tatacacacg tgggtcctgc aatgcaaaac      2940
atcatcaagc agttgtacct tcaccctgtt ccatattaa                             2979
```

<210> SEQ ID NO 4
<211> LENGTH: 1821
<212> TYPE: DNA
<213> ORGANISM: Artificial
<220> FEATURE:
<223> OTHER INFORMATION: Amorpho-4,11-diene synthase encoding cDNA of
      Artemisia annua linked to a plastid transit peptide sequence

<400> SEQUENCE: 4

```
atggcttcct ctatgctctc ctccgccgct gtggttacat ccccggctca ggccaccatg        60
gtcgctccat tcaccggctt gaagtcatcc gctgcattcc cggtcacccg caagaccaac       120
aaggacatca cttccatcgc aagcaacggg ggaagatcta gctgcatgaa gggcgcgccg       180
atgtcactta cagaagaaaa acctattcgc cccattgcca actttcctcc aagcatttgg       240
ggagatcagt ttctcatcta tgaaaagcaa gtagagcaag gggtggaaca gatagtgaat       300
gatttaaaaa aagaagtgcg gcaactacta aaagaagctt tggatattcc tatgaaacat       360
gccaatttat tgaagctgat tgatgaaatc caacgccttg gaataccgta tcactttgaa       420
cgggagattg atcatgcatt gcaatgtatt tatgaaacat atggtgataa ctggaatggt       480
gaccgctctt cctatggttc cgtcttatg cgaaagcaag atattatgt tacatgtgat        540 gtttcaata actataaaga caaaaatgga gcgttcaagc aatcgttagc taatgatgtt       600
gaaggtttgc ttgagttgta cgaagcaact tctatgaggg tacctgggga gattatatta       660
gaagatgctc ttggttttac acgatctcgt cttagcatta tgacaaaaga tgcttttct        720 acaaaccccg ctctttttac cgaaatacaa cgggcactaa agcaacccct ttggaaaagg       780
ttgccaagaa tagaggcggc gcagtacatt ccttctatc aacaacaaga ttctcataac        840
aagactttac ttaaacttgc taagttagag ttcaatttgc ttcagtcatt gcacaaggaa       900
gagctcagcc atgtgtgcaa atggtggaaa gctttcgata tcaagaagaa cgcaccttgt       960
ttaagagata gaattgttga atgctacttt tgggactag gttcaggcta tgagccacag       1020
tattcccggg ctagagtttt cttcacaaaa gctgttgctg ttataactct tatagatgac      1080
acttatgatg cgtatggtac ttatgaagaa cttaagatct ttactgaagc tgttgaaagg      1140
tggtcaatta catgcttaga cacacttcca gaatacatga aaccgatata caaattattc      1200
atggatacat acacagaaat ggaagaattt cttgcaaagg agggaagaac agatctattt      1260
aactgcggca agaatttgt gaaagagttt gttagaaacc tgatggttga agcaaaatgg      1320
gcaaatgagg gacacatacc aaccactgaa gagcatgatc cagttgtaat cattactggc      1380
ggtgctaacc tgcttacaac aacttgttat cttggcatga gtgatatatt cacaaaagag      1440
tctgtcgaat gggctgtctc tgcacctcct cttttagat actcaggtat acttggtcga      1500
cgcctaaatg atcctatgac ccacaaggcc gagcaagaaa gaaaacatag ttcatcgagc      1560
cttgaaagtt atatgaagga atataatgtc aatgaggagt atgcccaaac cttgatttac      1620
aaggaagtag aagatgtgtg gaaagatata aaccgagagt acctcacaac taaaaacatt      1680
ccaaggccgt tattgatggc tgtgatctat ttgtgccagt tccttgaagt tcaatatgca      1740
ggaaaggata acttcacacg tatgggagac gaatacaaac atctcataaa gtctctactc      1800
gtttatccta tgagtatatg a                                                1821
```

<210> SEQ ID NO 5
<211> LENGTH: 27

```
<212> TYPE: DNA
<213> ORGANISM: Artificial
<220> FEATURE:
<223> OTHER INFORMATION: Attp1-SstI-FW (Primer)

<400> SEQUENCE: 5
agtcacgagc tcgtaaaacg acggcca                                          27

<210> SEQ ID NO 6
<211> LENGTH: 23
<212> TYPE: DNA
<213> ORGANISM: Artificial
<220> FEATURE:
<223> OTHER INFORMATION: Attp2-SphI-RV (Primer)

<400> SEQUENCE: 6
gcatgccagg aaacagctat gac                                              23

<210> SEQ ID NO 7
<211> LENGTH: 26
<212> TYPE: DNA
<213> ORGANISM: Artificial
<220> FEATURE:
<223> OTHER INFORMATION: HPT-NotI-FD (Primer)

<400> SEQUENCE: 7
gcggccgcat gaaaaagcct gaactc                                           26

<210> SEQ ID NO 8
<211> LENGTH: 25
<212> TYPE: DNA
<213> ORGANISM: Artificial
<220> FEATURE:
<223> OTHER INFORMATION: HPT-Xba1-RV (Primer)

<400> SEQUENCE: 8
tctagataat tcgggggatc tggat                                            25

<210> SEQ ID NO 9
<211> LENGTH: 26
<212> TYPE: DNA
<213> ORGANISM: Artificial
<220> FEATURE:
<223> OTHER INFORMATION: TB-SphI- FD (Primer)

<400> SEQUENCE: 9
gtggttggca tgcacataca aatgga                                           26

<210> SEQ ID NO 10
<211> LENGTH: 26
<212> TYPE: DNA
<213> ORGANISM: Artificial
<220> FEATURE:
<223> OTHER INFORMATION: TB-NotI-RV (Primer)

<400> SEQUENCE: 10
gcggccgcgc gaaacgatcc agatcc                                           26

<210> SEQ ID NO 11
<211> LENGTH: 28
<212> TYPE: DNA
<213> ORGANISM: Artificial
<220> FEATURE:
<223> OTHER INFORMATION: HPT-SphI-RV (Primer)

<400> SEQUENCE: 11
ggggcatgct aattcggggg atctggat                                         28
```

<210> SEQ ID NO 12
<211> LENGTH: 56
<212> TYPE: DNA
<213> ORGANISM: Artificial
<220> FEATURE:
<223> OTHER INFORMATION: CSMV-ATTB1-SGFI-FD (Primer)

<400> SEQUENCE: 12
ggggacaagt ttgtacaaaa aagcaggctg cgatcgccct atgttcaaaa atgaag      56

<210> SEQ ID NO 13
<211> LENGTH: 31
<212> TYPE: DNA
<213> ORGANISM: Artificial
<220> FEATURE:
<223> OTHER INFORMATION: CSMV-ECORI-RV (Primer)

<400> SEQUENCE: 13
tacgaattca caaatttctc tgaagttgta t                                  31

<210> SEQ ID NO 14
<211> LENGTH: 31
<212> TYPE: DNA
<213> ORGANISM: Artificial
<220> FEATURE:
<223> OTHER INFORMATION: Tnos-XhoI-FW (Primer)

<400> SEQUENCE: 14
cggatgctcg aggatcgttc aaacatttgg c                                  31

<210> SEQ ID NO 15
<211> LENGTH: 49
<212> TYPE: DNA
<213> ORGANISM: Artificial
<220> FEATURE:
<223> OTHER INFORMATION: Tnos-attB2-RV (Primer)

<400> SEQUENCE: 15
ggggaccact ttgtacaaga aagctgggtg atctagtaac atagatgac              49

<210> SEQ ID NO 16
<211> LENGTH: 35
<212> TYPE: DNA
<213> ORGANISM: Artificial
<220> FEATURE:
<223> OTHER INFORMATION: His-EcoF (Primer)

<400> SEQUENCE: 16
aattcggcgc gccatgcatc atcatcatca tcacg                              35

<210> SEQ ID NO 17
<211> LENGTH: 35
<212> TYPE: DNA
<213> ORGANISM: Artificial
<220> FEATURE:
<223> OTHER INFORMATION: His-EcoR (Primer)

<400> SEQUENCE: 17
aattcgtgat gatgatgatg atgcatggcg cgccg                              35

<210> SEQ ID NO 18
<211> LENGTH: 44
<212> TYPE: DNA
<213> ORGANISM: Artificial
<220> FEATURE:
<223> OTHER INFORMATION: mHisPTS-F (Primer)

-continued

```
<400> SEQUENCE: 18
cttcagagaa atttgtgaat tatacatcat catcatcatc acgg          44

<210> SEQ ID NO 19
<211> LENGTH: 44
<212> TYPE: DNA
<213> ORGANISM: Artificial
<220> FEATURE:
<223> OTHER INFORMATION: mHisPTS-R (Primer)

<400> SEQUENCE: 19
ccgtgatgat gatgatgatg tataattcac aaatttctct gaag          44

<210> SEQ ID NO 20
<211> LENGTH: 31
<212> TYPE: DNA
<213> ORGANISM: Artificial
<220> FEATURE:
<223> OTHER INFORMATION: TP-ASCF (Primer)

<400> SEQUENCE: 20
ttggcgcgcc tatggcttcc tctatgctct c                        31

<210> SEQ ID NO 21
<211> LENGTH: 31
<212> TYPE: DNA
<213> ORGANISM: Artificial
<220> FEATURE:
<223> OTHER INFORMATION: TP-ASCR (Primer)

<400> SEQUENCE: 21
ttggcgcgcc cttcatgcag ctagatcttc c                        31

<210> SEQ ID NO 22
<211> LENGTH: 31
<212> TYPE: DNA
<213> ORGANISM: Artificial
<220> FEATURE:
<223> OTHER INFORMATION: PCaMV-XbaI-FW (Primer)

<400> SEQUENCE: 22
tcagtttcta gacatggagt caaagattca a                        31

<210> SEQ ID NO 23
<211> LENGTH: 27
<212> TYPE: DNA
<213> ORGANISM: Artificial
<220> FEATURE:
<223> OTHER INFORMATION: PCaMV-SpeI-RV (Primer)

<400> SEQUENCE: 23
accatgacta gtcccccgtg ttctctc                             27

<210> SEQ ID NO 24
<211> LENGTH: 28
<212> TYPE: DNA
<213> ORGANISM: Artificial
<220> FEATURE:
<223> OTHER INFORMATION: 7120D-SpeI-FW (Primer)

<400> SEQUENCE: 24
actagtatgc aattcttcag cttggttt                            28

<210> SEQ ID NO 25
<211> LENGTH: 33
```

```
<212> TYPE: DNA
<213> ORGANISM: Artificial
<220> FEATURE:
<223> OTHER INFORMATION: 7120D-KpnI-RV (Primer)

<400> SEQUENCE: 25
cggggtacct tactcccgag aaggttgata agg                               33

<210> SEQ ID NO 26
<211> LENGTH: 28
<212> TYPE: DNA
<213> ORGANISM: Artificial
<220> FEATURE:
<223> OTHER INFORMATION: Tnos-KpnI-FW (Primer)

<400> SEQUENCE: 26
cggggtaccg atcgttcaaa catttggc                                     28

<210> SEQ ID NO 27
<211> LENGTH: 21
<212> TYPE: DNA
<213> ORGANISM: Artificial
<220> FEATURE:
<223> OTHER INFORMATION: Tnos-attB2-RV3 (Primer)

<400> SEQUENCE: 27
gagctcgggg accactttgt a                                            21

<210> SEQ ID NO 28
<211> LENGTH: 56
<212> TYPE: DNA
<213> ORGANISM: Artificial
<220> FEATURE:
<223> OTHER INFORMATION: CsMV-attB1-Sgf I-FD (Primer)

<400> SEQUENCE: 28
ggggacaagt ttgtacaaaa aagcaggctg cgatcgccct atgttcaaaa atgaag      56

<210> SEQ ID NO 29
<211> LENGTH: 28
<212> TYPE: DNA
<213> ORGANISM: Artificial
<220> FEATURE:
<223> OTHER INFORMATION: TNOS-XbaI-RV (Primer)

<400> SEQUENCE: 29
gctctagaga tctagtaaca tagatgac                                     28

<210> SEQ ID NO 30
<211> LENGTH: 30
<212> TYPE: DNA
<213> ORGANISM: Artificial
<220> FEATURE:
<223> OTHER INFORMATION: TP-SpeFW (Primer)

<400> SEQUENCE: 30
ggggactagt atggcttcct ctatgctctc                                   30

<210> SEQ ID NO 31
<211> LENGTH: 31
<212> TYPE: DNA
<213> ORGANISM: Artificial
<220> FEATURE:
<223> OTHER INFORMATION: TP-SpeRV (Primer)

<400> SEQUENCE: 31
ggggactagt cttcatgcag ctagatcttc c                                 31
```

<210> SEQ ID NO 32
<211> LENGTH: 34
<212> TYPE: DNA
<213> ORGANISM: Artificial
<220> FEATURE:
<223> OTHER INFORMATION: PTS-AscF (Primer)

<400> SEQUENCE: 32
ggggagctcg gcgcgccgat ggagttgtat gccc                     34

<210> SEQ ID NO 33
<211> LENGTH: 31
<212> TYPE: DNA
<213> ORGANISM: Artificial
<220> FEATURE:
<223> OTHER INFORMATION: PTS-XhoR (Primer)

<400> SEQUENCE: 33
ggggctcgag ttaatatgga acagggtgaa g                        31

<210> SEQ ID NO 34
<211> LENGTH: 35
<212> TYPE: DNA
<213> ORGANISM: Artificial
<220> FEATURE:
<223> OTHER INFORMATION: FPP-SpeFW (Primer)

<400> SEQUENCE: 34
ggggactagt atgcagcccc atcatcatca taaag                    35

<210> SEQ ID NO 35
<211> LENGTH: 31
<212> TYPE: DNA
<213> ORGANISM: Artificial
<220> FEATURE:
<223> OTHER INFORMATION: FPP-KpnRV (Primer)

<400> SEQUENCE: 35
cggggtacct catttctggc gtttgtagat c                        31

<210> SEQ ID NO 36
<211> LENGTH: 30
<212> TYPE: DNA
<213> ORGANISM: Artificial
<220> FEATURE:
<223> OTHER INFORMATION: FPS-AscF (Primer)

<400> SEQUENCE: 36
ttggcgcgcc tatgcagccc catcatcatc                          30

<210> SEQ ID NO 37
<211> LENGTH: 30
<212> TYPE: DNA
<213> ORGANISM: Artificial
<220> FEATURE:
<223> OTHER INFORMATION: FPS-AscR (Primer)

<400> SEQUENCE: 37
ttggcgcgcc ttttctggcg tttgtagatc                          30

<210> SEQ ID NO 38
<211> LENGTH: 24
<212> TYPE: DNA
<213> ORGANISM: Artificial
<220> FEATURE:
<223> OTHER INFORMATION: PTS-8F (Primer)

```
<400> SEQUENCE: 38
gagtgggtgc tgcttctcgt cctc                                          24

<210> SEQ ID NO 39
<211> LENGTH: 24
<212> TYPE: DNA
<213> ORGANISM: Artificial
<220> FEATURE:
<223> OTHER INFORMATION: PTS-160R (Primer)

<400> SEQUENCE: 39
ctccatggac tctgagatgc gtgg                                          24

<210> SEQ ID NO 40
<211> LENGTH: 26
<212> TYPE: DNA
<213> ORGANISM: Artificial
<220> FEATURE:
<223> OTHER INFORMATION: FPP-1F (Primer)

<400> SEQUENCE: 40
gcagccccat catcatcata aagagg                                        26

<210> SEQ ID NO 41
<211> LENGTH: 23
<212> TYPE: DNA
<213> ORGANISM: Artificial
<220> FEATURE:
<223> OTHER INFORMATION: FPP-160R58 (Primer)

<400> SEQUENCE: 41
gaggactcga ggaggaagga gtc                                           23

<210> SEQ ID NO 42
<211> LENGTH: 21
<212> TYPE: DNA
<213> ORGANISM: Artificial
<220> FEATURE:
<223> OTHER INFORMATION: RBCS-FW (Primer)

<400> SEQUENCE: 42
atgcaggtgt ggccaccaat t                                             21

<210> SEQ ID NO 43
<211> LENGTH: 21
<212> TYPE: DNA
<213> ORGANISM: Artificial
<220> FEATURE:
<223> OTHER INFORMATION: RBCS-RV (Primer)

<400> SEQUENCE: 43
ttagtagcct tctggcttgt a                                             21

<210> SEQ ID NO 44
<211> LENGTH: 34
<212> TYPE: DNA
<213> ORGANISM: Artificial
<220> FEATURE:
<223> OTHER INFORMATION: ADS-AscF (Primer)

<400> SEQUENCE: 44
ttggcgcgcc gatgtcactt acagaagaaa aacc                               34

<210> SEQ ID NO 45
<211> LENGTH: 34
```

```
<212> TYPE: DNA
<213> ORGANISM: Artificial
<220> FEATURE:
<223> OTHER INFORMATION: ADS-XhoR (Primer)

<400> SEQUENCE: 45
ggggctcgag tcatatactc ataggataaa cgag                                    34

<210> SEQ ID NO 46
<211> LENGTH: 43
<212> TYPE: DNA
<213> ORGANISM: Artificial
<220> FEATURE:
<223> OTHER INFORMATION: pLlinkF (Primer)

<400> SEQUENCE: 46
aattgcgatc gcggattcac tagtgcggcc gccccggggg tac                          43

<210> SEQ ID NO 47
<211> LENGTH: 35
<212> TYPE: DNA
<213> ORGANISM: Artificial
<220> FEATURE:
<223> OTHER INFORMATION: pLlinkR (Primer)

<400> SEQUENCE: 47
ccccggggcg gccgcactag tgaatccgcg atcgc                                   35

<210> SEQ ID NO 48
<211> LENGTH: 26
<212> TYPE: DNA
<213> ORGANISM: Artificial
<220> FEATURE:
<223> OTHER INFORMATION: attP-XbaF (Primer)

<400> SEQUENCE: 48
gctctagaga gcaatcgccc tgggtg                                             26

<210> SEQ ID NO 49
<211> LENGTH: 28
<212> TYPE: DNA
<213> ORGANISM: Artificial
<220> FEATURE:
<223> OTHER INFORMATION: Attp-SphR (Primer)

<400> SEQUENCE: 49
gggggcatgc cccggtcaca accccttg                                           28

<210> SEQ ID NO 50
<211> LENGTH: 28
<212> TYPE: DNA
<213> ORGANISM: Artificial
<220> FEATURE:
<223> OTHER INFORMATION: Prrn-XbaF (Primer)

<400> SEQUENCE: 50
gctctagaag agtgtcacct tgacgtgg                                           28

<210> SEQ ID NO 51
<211> LENGTH: 30
<212> TYPE: DNA
<213> ORGANISM: Artificial
<220> FEATURE:
<223> OTHER INFORMATION: TrbcL -KpnR (Primer)

<400> SEQUENCE: 51
ggggtaccgt attcggctca atccttttag                                         30
```

<210> SEQ ID NO 52
<211> LENGTH: 28
<212> TYPE: DNA
<213> ORGANISM: Artificial
<220> FEATURE:
<223> OTHER INFORMATION: Prrn-KpnF (Primer)

<400> SEQUENCE: 52
ggggtaccag agtgtcacct tgacgtgg                                28

<210> SEQ ID NO 53
<211> LENGTH: 28
<212> TYPE: DNA
<213> ORGANISM: Artificial
<220> FEATURE:
<223> OTHER INFORMATION: Prrn-SmaR (Primer)

<400> SEQUENCE: 53
tcccccggga aatccctccc tacaactg                                28

<210> SEQ ID NO 54
<211> LENGTH: 29
<212> TYPE: DNA
<213> ORGANISM: Artificial
<220> FEATURE:
<223> OTHER INFORMATION: Tatp-SmaF (Primer)

<400> SEQUENCE: 54
tcccccggga gaaatattga tcacttttg                               29

<210> SEQ ID NO 55
<211> LENGTH: 31
<212> TYPE: DNA
<213> ORGANISM: Artificial
<220> FEATURE:
<223> OTHER INFORMATION: Tatp-NotR (Primer)

<400> SEQUENCE: 55
ggggcggccg catttatttc catatatatt t                            31

<210> SEQ ID NO 56
<211> LENGTH: 31
<212> TYPE: DNA
<213> ORGANISM: Artificial
<220> FEATURE:
<223> OTHER INFORMATION: LacI-SmaF (Primer)

<400> SEQUENCE: 56
tcccccggga tgaaaccagt aacgttatac g                            31

<210> SEQ ID NO 57
<211> LENGTH: 30
<212> TYPE: DNA
<213> ORGANISM: Artificial
<220> FEATURE:
<223> OTHER INFORMATION: LacI-SmaR (Primer)

<400> SEQUENCE: 57
tcccccgggt cactgcccgc tttccagtcg                              30

<210> SEQ ID NO 58
<211> LENGTH: 32
<212> TYPE: DNA
<213> ORGANISM: Artificial
<220> FEATURE:
<223> OTHER INFORMATION: Trbcl-SpeF (Primer)

```
<400> SEQUENCE: 58
ggactagtaa aacagtagac attagcagat aa                                    32

<210> SEQ ID NO 59
<211> LENGTH: 34
<212> TYPE: DNA
<213> ORGANISM: Artificial
<220> FEATURE:
<223> OTHER INFORMATION: Trbcl-NotR (Primer)

<400> SEQUENCE: 59
gggggcggcc gcgtattcgg ctcaatcctt ttag                                  34

<210> SEQ ID NO 60
<211> LENGTH: 33
<212> TYPE: DNA
<213> ORGANISM: Artificial
<220> FEATURE:
<223> OTHER INFORMATION: PrrnlacI-SgfF (Primer)

<400> SEQUENCE: 60
ggggcgatcg cagagtgtca ccttgacgtg gtg                                   33

<210> SEQ ID NO 61
<211> LENGTH: 60
<212> TYPE: DNA
<213> ORGANISM: Artificial
<220> FEATURE:
<223> OTHER INFORMATION: PrrnlacI-R1nest (Primer)

<400> SEQUENCE: 61
attcgcccgg agttcgctcc cagaaatata ttgttatccg ctcacaatcg tcaatcccac      60

<210> SEQ ID NO 62
<211> LENGTH: 59
<212> TYPE: DNA
<213> ORGANISM: Artificial
<220> FEATURE:
<223> OTHER INFORMATION: PrrnlacI-BamHR (Primer)

<400> SEQUENCE: 62
cgggatccaa atccctccct acaactgtat ccaagcgctt cgtattcgcc cggagttcg       59

<210> SEQ ID NO 63
<211> LENGTH: 29
<212> TYPE: DNA
<213> ORGANISM: Artificial
<220> FEATURE:
<223> OTHER INFORMATION: GUS-BamF (Primer)

<400> SEQUENCE: 63
cgggattcat gttacgtcct gtagaaacc                                        29

<210> SEQ ID NO 64
<211> LENGTH: 30
<212> TYPE: DNA
<213> ORGANISM: Artificial
<220> FEATURE:
<223> OTHER INFORMATION: GUS-SpeR (Primer)

<400> SEQUENCE: 64
ggactagttc attgtttgcc tccctgctgc                                       30

<210> SEQ ID NO 65
<211> LENGTH: 33
```

```
<212> TYPE: DNA
<213> ORGANISM: Artificial
<220> FEATURE:
<223> OTHER INFORMATION: FPS-BamF (Primer)

<400> SEQUENCE: 65
cgggattcat gcagccccat catcatcata aag                              33

<210> SEQ ID NO 66
<211> LENGTH: 29
<212> TYPE: DNA
<213> ORGANISM: Artificial
<220> FEATURE:
<223> OTHER INFORMATION: PTS-SpeR (Primer)

<400> SEQUENCE: 66
ggactagttt aatatggaac agggtgaag                                   29

<210> SEQ ID NO 67
<211> LENGTH: 30
<212> TYPE: DNA
<213> ORGANISM: Artificial
<220> FEATURE:
<223> OTHER INFORMATION: Trbcl-AscF (Primer)

<400> SEQUENCE: 67
ttggcgcgcc aaaacagtag acattagcag                                  30

<210> SEQ ID NO 68
<211> LENGTH: 30
<212> TYPE: DNA
<213> ORGANISM: Artificial
<220> FEATURE:
<223> OTHER INFORMATION: Trbcl-SpeR (Primer)

<400> SEQUENCE: 68
ggactagtgt attcggctca atccttttag                                  30

<210> SEQ ID NO 69
<211> LENGTH: 30
<212> TYPE: DNA
<213> ORGANISM: Artificial
<220> FEATURE:
<223> OTHER INFORMATION: PrrnlacI-SpeF (Primer)

<400> SEQUENCE: 69
ggactagtag agtgtcacct tgacgtggtg                                  30

<210> SEQ ID NO 70
<211> LENGTH: 40
<212> TYPE: DNA
<213> ORGANISM: Artificial
<220> FEATURE:
<223> OTHER INFORMATION: Prrnlac-AscI-SpeR (Primer)

<400> SEQUENCE: 70
ggactagtgg cgcgccaaat ccctccctac aactgtatcc                       40

<210> SEQ ID NO 71
<211> LENGTH: 7
<212> TYPE: PRT
<213> ORGANISM: Artificial
<220> FEATURE:
<223> OTHER INFORMATION: PTS46 antigenic peptide

<400> SEQUENCE: 71

Glu Glu Leu Lys Val Glu Leu
```

```
<210> SEQ ID NO 72
<211> LENGTH: 20
<212> TYPE: PRT
<213> ORGANISM: Artificial
<220> FEATURE:
<223> OTHER INFORMATION: PTS108 antigenic peptide

<400> SEQUENCE: 72

His Ala Thr Ala Leu Ser Phe Arg Leu Leu Arg Gln His Gly Tyr Arg
1               5                   10                  15

Val Ser Cys Glu
            20

<210> SEQ ID NO 73
<211> LENGTH: 13
<212> TYPE: PRT
<213> ORGANISM: Artificial
<220> FEATURE:
<223> OTHER INFORMATION: PTS353 antigenic peptide

<400> SEQUENCE: 73

Asp Glu Glu Leu Ile Lys Leu Gly Ala Pro Tyr Arg Ala
1               5                   10

<210> SEQ ID NO 74
<211> LENGTH: 11
<212> TYPE: PRT
<213> ORGANISM: Artificial
<220> FEATURE:
<223> OTHER INFORMATION: PTS462 antigenic peptide

<400> SEQUENCE: 74

His Val Arg Thr Ala Val Glu Cys Tyr Met Glu
1               5                   10

<210> SEQ ID NO 75
<211> LENGTH: 10
<212> TYPE: PRT
<213> ORGANISM: Artificial
<220> FEATURE:
<223> OTHER INFORMATION: PTS475 antigenic peptide

<400> SEQUENCE: 75

Lys Val Gly Lys Gln Glu Val Val Ser Glu
1               5                   10

<210> SEQ ID NO 76
<211> LENGTH: 11
<212> TYPE: PRT
<213> ORGANISM: Artificial
<220> FEATURE:
<223> OTHER INFORMATION: FPP41 antigenic peptide

<400> SEQUENCE: 76

Glu Phe Val Gly Phe Phe Pro Gln Ile Val Arg
1               5                   10

<210> SEQ ID NO 77
<211> LENGTH: 18
<212> TYPE: PRT
<213> ORGANISM: Artificial
<220> FEATURE:
<223> OTHER INFORMATION: FPP59 antigenic peptide

<400> SEQUENCE: 77
```

-continued

```
Gly His Pro Glu Val Gly Asp Ala Val Ala Arg Leu Lys Glu Val Leu
1               5                   10                  15

Gln Tyr

<210> SEQ ID NO 78
<211> LENGTH: 20
<212> TYPE: PRT
<213> ORGANISM: Artificial
<220> FEATURE:
<223> OTHER INFORMATION: FPP218 antigenic peptide

<400> SEQUENCE: 78

Tyr Lys Ala Ile Val Lys Tyr Lys Thr Ala Phe Tyr Ser Phe Tyr Leu
1               5                   10                  15

Pro Val Ala Ala
            20

<210> SEQ ID NO 79
<211> LENGTH: 13
<212> TYPE: PRT
<213> ORGANISM: Artificial
<220> FEATURE:
<223> OTHER INFORMATION: FPP320 antigenic peptide

<400> SEQUENCE: 79

Pro Glu Lys Val Ala Lys Val Lys Glu Leu Tyr Glu Ala
1               5                   10
```